US008636986B2

(12) United States Patent
Van Dyke

(10) Patent No.: US 8,636,986 B2
(45) Date of Patent: Jan. 28, 2014

(54) TREATMENT AND PREVENTION OF BONE LOSS USING RESOLVINS

(75) Inventor: Thomas E. Van Dyke, West Roxbury, MA (US)

(73) Assignee: The Forsyth Institute, Cambridge, MA (US)

( * ) Notice: Subject to any disclaimer, the term of this patent is extended or adjusted under 35 U.S.C. 154(b) by 590 days.

(21) Appl. No.: 12/094,016

(22) PCT Filed: Nov. 17, 2006

(86) PCT No.: PCT/US2006/044556
§ 371 (c)(1),
(2), (4) Date: Jul. 11, 2008

(87) PCT Pub. No.: WO2007/061783
PCT Pub. Date: May 31, 2007

(65) Prior Publication Data
US 2008/0280980 A1 Nov. 13, 2008

Related U.S. Application Data

(60) Provisional application No. 60/738,328, filed on Nov. 18, 2005.

(51) Int. Cl.
*A61K 8/00* (2006.01)
(52) U.S. Cl.
USPC .......................................................... 424/49
(58) Field of Classification Search
USPC .......................................................... 424/49
See application file for complete search history.

(56) References Cited

U.S. PATENT DOCUMENTS

| | | |
|---|---|---|
| 4,201,211 A | 5/1980 | Chandrasekaran et al. |
| 4,442,099 A | 4/1984 | Nicolaou et al. |
| 4,567,290 A | 1/1986 | Nicolaou et al. |
| 4,576,758 A | 3/1986 | Morris et al. |
| 4,666,701 A | 5/1987 | Horrobin et al. |
| 4,710,521 A | 12/1987 | Soukup et al. |
| 4,759,880 A | 7/1988 | Nicolaou et al. |
| 4,810,424 A | 3/1989 | Gerwick et al. |
| 5,087,790 A | 2/1992 | Petasis et al. |
| 5,136,501 A | 8/1992 | Silverman et al. |
| 5,177,046 A | 1/1993 | Savoca et al. |
| 5,374,431 A * | 12/1994 | Pang et al. ..................... 424/486 |
| 5,409,955 A | 4/1995 | Bockow et al. |
| 5,411,988 A | 5/1995 | Bockow et al. |
| 5,441,951 A | 8/1995 | Serhan |
| 5,594,732 A | 1/1997 | Bell et al. |
| 5,604,258 A | 2/1997 | Ferrante et al. |
| 5,648,512 A | 7/1997 | Serhan |
| 5,652,227 A * | 7/1997 | Teronen et al. ................. 514/75 |
| 5,709,855 A | 1/1998 | Bockow |
| 5,752,238 A | 5/1998 | Dedrick |
| 5,756,789 A | 5/1998 | Bruce et al. |
| 5,814,599 A | 9/1998 | Mitragotri et al. |
| 5,842,040 A | 11/1998 | Hughes et al. |
| 5,845,265 A | 12/1998 | Woolston |
| 5,846,974 A | 12/1998 | Kallman et al. |
| 5,861,399 A | 1/1999 | Seed et al. |
| 5,870,717 A | 2/1999 | Wiecha |
| 5,878,400 A | 3/1999 | Carter, III |
| 5,878,423 A | 3/1999 | Anderson et al. |
| 5,890,138 A | 3/1999 | Godin et al. |
| 5,896,379 A | 4/1999 | Haber |
| 5,912,006 A | 6/1999 | Bockow et al. |
| 5,932,598 A | 8/1999 | Talley et al. |
| 5,946,467 A | 8/1999 | Pathakis et al. |
| 6,030,715 A | 2/2000 | Thompson et al. |
| 6,030,917 A | 2/2000 | Weinberg et al. |
| 6,048,897 A | 4/2000 | Serhan |
| 6,069,109 A | 5/2000 | Kao et al. |
| 6,117,911 A | 9/2000 | Grainger et al. |
| 6,201,022 B1 | 3/2001 | Mease et al. |
| 6,232,467 B1 | 5/2001 | Petasis et al. |
| 6,259,699 B1 | 7/2001 | Opalka et al. |
| 6,272,474 B1 | 8/2001 | Garcia |
| 6,316,648 B1 | 11/2001 | Serhan |
| 6,336,105 B1 | 1/2002 | Conklin et al. |
| 6,336,138 B1 | 1/2002 | Caswell et al. |
| 6,377,937 B1 | 4/2002 | Paskowitz |

(Continued)

FOREIGN PATENT DOCUMENTS

| | | |
|---|---|---|
| EP | 0736509 | 10/1996 |
| GB | 2033745 | 5/1979 |

(Continued)

OTHER PUBLICATIONS

Scope and Editorial Policy, *Organometallics* 21(1):13A 14A (2002).
De Montarby et al., "Synthese stereoselectives de metabolite hydroxyles d'acides gras polyinsatures," *Bulletin De La Societe Chimique de France*, No. 3, pp. 419-432, 1989 (English abstract).
Database WPI, *Sedm Ch*, Week 199334. Derwent Publications Ltd., London, GB; AN 1993-269748. XP002184773. (see also JP 05186342, Jul. 27, 1993).
Alami, et al., "A versatile route to conjugated hydroxy (E,Z,E,E)-tetraenoic acids: highly chemo- and stereoselective synthesis of lipoxin 84 tetrahedro", *Asym.* 8(17)2949-2958, 1997.
Albert. C.M., et al., Blood levels of long-chain n-e fatty acids and the risk of sudden death, *N. Engl. J. Med.* vol. 346, pp. 1113-1138, 2002.
Arita et al., "Stereochemical Assignment, Antiinflammatory Properties, and Receptor for the Omega-3 Lipid Mediator Resolvin El", *J. Exp, Med*, 201(5): 713-722, 2005.

(Continued)

*Primary Examiner* — Frederick Krass
*Assistant Examiner* — Adam C Milligan
(74) *Attorney, Agent, or Firm* — Foley Hoag LLP

(57) ABSTRACT

The present invention provides new methods for inducing or promoting bone growth and/or for reducing or preventing bone deterioration in a mammal subject. The inventive methods generally comprise administering to the subject an effective amount of a resolvin. In particular, the inventive methods may be useful for treating or preventing conditions associated with bone degradation, deterioration or degeneration such as periodontal disease, osteoarthritis, and metastatic bone disease and osteolytic bone disease. Pharmaceutical compositions and kits comprising at least one resolvin are also provided that can be used to performed the inventive methods.

7 Claims, 7 Drawing Sheets

(56) References Cited

U.S. PATENT DOCUMENTS

| | | |
|---|---|---|
| 6,397,212 B1 | 5/2002 | Biffar |
| 6,415,270 B1 | 7/2002 | Rackson et al. |
| 6,427,132 B1 | 7/2002 | Bowman-Amuah |
| 6,428,990 B1 | 8/2002 | Mukerji et al. |
| 6,569,075 B2 | 5/2003 | Serhan |
| 6,602,817 B1 | 8/2003 | Petasis |
| 6,620,919 B2 | 9/2003 | Serhan |
| 6,635,776 B2 | 10/2003 | Serhan |
| 6,653,493 B2 | 11/2003 | Serhan |
| 6,670,396 B2 | 12/2003 | Serhan et al. |
| 6,750,360 B2 | 6/2004 | Serhan |
| 6,887,901 B1 | 5/2005 | Serhan |
| 6,949,664 B2 | 9/2005 | Petasis |
| 7,030,159 B2 | 4/2006 | Serhan et al. |
| 7,053,230 B2 | 5/2006 | Serhan et al. |
| 7,341,840 B2 | 3/2008 | Serhan et al. |
| 2001/0023500 A1 | 9/2001 | Serhan |
| 2001/0031882 A1 | 10/2001 | Serhan |
| 2002/0010351 A1 | 1/2002 | Serhan |
| 2002/0045579 A1 | 4/2002 | Madara et al. |
| 2002/0055538 A1 | 5/2002 | Serhan et al. |
| 2002/0082435 A1 | 6/2002 | Serhan |
| 2002/0091279 A1 | 7/2002 | Serhan |
| 2002/0094549 A1 | 7/2002 | Serhan et al. |
| 2002/0107289 A1 | 8/2002 | Serhan |
| 2002/0111505 A1 | 8/2002 | Serhan |
| 2002/0120013 A1 | 8/2002 | Serhan |
| 2002/0132847 A1 | 9/2002 | Serhan |
| 2002/0143069 A1 | 10/2002 | Serhan |
| 2002/0193431 A1 | 12/2002 | Serhan et al. |
| 2003/0032827 A1 | 2/2003 | Serhan |
| 2003/0055275 A1 | 3/2003 | Serhan |
| 2003/0060512 A1 | 3/2003 | Madara et al. |
| 2003/0069435 A1 | 4/2003 | Serhan |
| 2003/0134901 A1 | 7/2003 | Serhan |
| 2003/0166716 A1 | 9/2003 | Serhan et al. |
| 2003/0191184 A1 | 10/2003 | Serhan et al. |
| 2003/0191332 A1 | 10/2003 | Serhan et al. |
| 2003/0195248 A1 | 10/2003 | Serhan et al. |
| 2003/0236423 A1 | 12/2003 | Petasis |
| 2004/0019110 A1 | 1/2004 | Van Dyke et al. |
| 2004/0044050 A1 | 3/2004 | Goodman et al. |
| 2004/0053998 A1 | 3/2004 | Serhan et al. |
| 2004/0059144 A1 | 3/2004 | Serhan et al. |
| 2004/0116408 A1 | 6/2004 | Serhan |
| 2004/0151712 A1 | 8/2004 | Madara et al. |
| 2004/0192785 A1 | 9/2004 | Serhan |
| 2005/0075398 A1 | 4/2005 | Bazan et al. |
| 2005/0228047 A1 | 10/2005 | Petasis |
| 2005/0238589 A1 | 10/2005 | Van Dyke et al. |
| 2005/0261255 A1 | 11/2005 | Serhan et al. |
| 2006/0128804 A1 | 6/2006 | Serhan et al. |
| 2006/0293288 A1 | 12/2006 | Serhan et al. |

FOREIGN PATENT DOCUMENTS

| | | |
|---|---|---|
| JP | 5186342 | 7/1993 |
| WO | WO 91/16914 | 11/1991 |
| WO | WO 97/19415 | 5/1997 |
| WO | WO 98/19259 | 5/1998 |
| WO | WO 98/35469 | 8/1998 |
| WO | WO 98/46588 | 10/1998 |
| WO | WO 99/06913 | 2/1999 |
| WO | WO 99/13417 | 3/1999 |
| WO | WO 99/56727 | 11/1999 |
| WO | WO 00/32210 | 6/2000 |
| WO | WO 01/60778 | 8/2001 |
| WO | WO 03/051350 | 6/2003 |
| WO | WO 03/053423 | 7/2003 |
| WO | WO 03/084305 | 10/2003 |
| WO | WO 03/105776 | 12/2003 |
| WO | WO 2004/014835 | 2/2004 |
| WO | WO 2005/089744 | 9/2005 |

OTHER PUBLICATIONS

Arita, et al. "Resolvin E1. an Endogenous Lipid Mediator Derived from Omega-3 Eicosapentaenoic Acid, Protects Against 2. 4, 6-Trinitrobenzene Sufonic Acid-Induced Colitis", *Proc. Natl. Acad. Sci. USA*, 102(21) 7671-7676, 2005.

Babine, R.E. and S.L.Bender., "Molecular Recognition of protein-Ligand Complexes: Applications to Design" *Chem. Rev.* 97:1359-1472 (1997).

Bandeira-Melo. C., et. al,. "Cyclooxygenase-2-derived prostaglandin $E_2$ and lipoxin $A_4$. accelerate resolution of allergic edema in *Antiostrongylus* costaricensis infected rats: relationship with concurrent eosinophilia", *J. Immunol*, vol. 164, pp. 1029-1036, 2000.

Bannenberg, et al., "Molecular Circuits of Resolution: Formation and Actions of Resolvins and Prolectins", *Immunol.* 174(7): 4345-4355, 2005.

Bazan, N.G., et al., Docosahexaneoic acid (22:6,n-3) is metabolized to lipoxygenase reaction products in the retina_ , *Biochem. Biophys. Res. Commun.*,, vol. 125, pp. 741-747, 1984.

Bazan, N.G., et al., "Pathways for the uptake and conservation of docosahexaenoic acid in photoreceptors and synapses: biochemical and autoradiographic studies", *Cn. J. Physiol. Pharmacol* .vol. 71, pp. 690-698, 1993.

Beamer, L.J., et al., "Crystal structure of human BPI and two bound phospholipids at 2.4 angstrom resolution", *Science* vol. 276, 1997, pp. 1861-1864.

Bhaley, G. et al., "Solid Phase Synthesis of Diverse Tetrahydro-1,4-Benzodiazepine-2-ones," Tetrahedron Letters 38(48):8375-8378 (1997).

Billman, G.E. et al., "Prevention of sudden cardiac death by dietary pure w-3 polyunsaturated fatty acids in dogs", *Circulation* 99 1999, pp. 2452-2457.

Blaser, E. et al., "Asymmetrix Steering of oxa Diels—Alder Reactions with Silyloxydienes Employing Proline Esters as Chiral Auxiliary Groups," *Eur. J. Org. Chem.*, 329-333. 1999).

Boland, et al., "Stereospecific Syntheses and Spectroscopis Properties of Isomeric 2,4,6,8—Undecatetraenes New Hydrocarbons from the Marine Brown Alga *Giffordia mitchellae*", *Helv. Chim. Acta.*, 70:1025-1040, 1987.

Booyens, J. et al., "Some effects of the essential fatty acids linoleic acid and alpha-linolenic acid and of their metabolites gamma-linolenic acid, arachidonic acid, eicosapentaenoic acid, docosahexaenoic acid, and of prostaglandins Al and E1 on the proliferation of human osteogenic sarcoma cells in culture", Prostaglandins *Leukot Med.*, vol. 15, pp. 15-33, 1984.

Buchanan, M•R., et al.. "Regulation of endothelial cell and platelet receptor-ligand binding by the 12- and 15-lipoxygenase monohydroxides, 12-, 15-HETE and 13-HODE", *Prostaglandins Letikot Essent. Fatty Acids* 1998, pp. 339-346.

Canny, G., et al., "Lipid mediator-induced expression of bactericidal/ permeability-increasing protein (BPI) in human mucosal epithelia", *Proc. Natl. Acad. Sci. USA*. vol. 99, pp. 3902-3907, 2002.

Capdevila, J.H., et al., "The highly stereoselective oxidation of poly-unsaturated fatty acids by cytochrome P450BM-3", *J. Biol. Chem.* 1996, pp. 22663-22671.

Catella-Lawson, J., et al., "Cyclooxygenase inhibitors and the antiplatelet effects of aspirin", *N. Engl. J. Med.*, vol. 345, pp. 1809-1817, 2001.

Chiang, N., et al., "Aspirin-triggered 15-epi-lipoxin $A_4$ (ATL) generation by human leukocytes and murine peritonitis exudates: Development of a specific 15-epi-LXA4 ELISA", *J. Pharmacol. Exp. Thor.* 1998. pp. 779-790.

Chiang, N., et al., "Leukotriene B4 receptor transgenic mice reveal novel protective roles for lipoxins and aspirin-triggered lipoxins in reperfusion", *J. Clin. Invest.* 1999, pp. 309-316.

Claria, J. et al., -"Aspirin triggers previously undescribed bioactive eicosanoids by human endothelial cell-leukocyte interactions", *Proc. Natl. Acad. Sci. USA* 1995. pp. 9475-9479.

Clish. C.B., et al. "Oxidoreductases in lipoxin $A_4$, metabolic inactivation". *J. Biol. Chem..* vol. 375, pp. 25372-25380, 2000.

Colgan, S.P. et al., "Defective invitro motility of polymorphonuclear leukocytes of homozygote and heterozygote Chediak-higashi cats", *Vet. Immunol. Immunopathology*, 1992, pp. 205-227.

(56) References Cited

OTHER PUBLICATIONS

Colgan, S.P., et al., "Lipoxin A$_4$ modulates transmigration of human neutrophils across intestinal epithelial monolayers", *J. Clin. Invest.*, vol. 92, pp. 75-82, 1993.
Cooper, S.F., et al.. "Identification of Antibacterial Fatty Acids from Phaeodactylum tricomtum grown i dialysis culture", *The Faculty Press*, 1985, pp. 28-36.
Corey, E.J., et al., "Docosahexaenoic acid is a strong inhibitor of prostaglandin but not leukotriene biosynthesis", *Proc. Natl. Acad. Sci. USA*, vol. 80, pp. 3581-3584, 1983.
Crofford. L.J., "Rational use of analgesic and antiinflammatory drugs", *Engl. J. Med.*, vol. 345, pp. 1844-1846, 2001.
Cronstein, B.N., et al., "A mechanism for the anti-inflammatory effects of corticosteriods: The glucocorticoid receptor regulates leukocyte adhesion to endothelial cells and expression of endothelial-leukocyte adhesion molecule 1 and intercellular adhesion molecule 1", *Proc. Natl. Acad. Sci.* 1992, pp. 9991-9995.
Croset, M. et al., "Inhibition by Lipoxygenase Products of TXA2-Like Responses of Platelets and Vascular Smooth Muscle", Biochemical Pharmacology, vol. 37, No. 7, pp. 1275-1280, 1988, XP0024-45509.
De Caterina, R., et al., "n-e Fatty Acids and Vascular Disease", *Current Topics in Cardiovascular Disease*, Springler-Verlag, London, 1993.
De Montarby, L., et al. "Synthesis stereoselectives de metabolites hydroxyles d'acides gras polinsatures", *Bulletin De La Societe Chimique de France*. No. 3. pp. 419-432, 1989.
Dharmsathaphorn, K., et al., "Established intestinal cell lines as model systems for electrolyte transport studies", *Methods in Enzymology*, vol. 192, 1990, pp. 354-389.
Dioux, Laurent and Morris Srebnik, "Asymmetric Boron-Catalyzed Reactions", Chem. Rev. 93:763-784, (1993).
Drazen, J.M., et al., "Heterogeneity of therapeutic responses in asthma", *Br. Med. Bull*, vol. 56, pp. 1054-1070, 2000.
Durantel, et al., "Study of the mechanism of Antiviral Action of Iminosugar Derivatives against Bovine Viral Diarrhea Virus," *J. Virology* 75(19): 8987-8998, (2001).
Du Bois (Vu Bois?), et al., "novel, Stereoselective Synthesis of 2 Amino Saccharides," *J. Am. Chem. Soc.* 119: 3179-3180. 1997.
Eckmann, L., et al., "Epithelial cells secrete the chemokine interleukin-8 in response to bacterial entry", *Infection and Immunity*, vol. 61, No. 11, 1193, pp. 4569-4574.
Elsbach, P. et al., "Role of the bactericidal/permeability-increasing protein in host defence", *Current Opinion in Immunology*, vol. 10, No. 1, 1998, pp. 45-49.
Eritsland. et al , "Effects of Highly Concentrated Omega-3 PUF as and Acetylsalicylic Acid, Alone and Combined, on Bleeding Time and Serum Liquid Profile", *J. Olso City Hosp.*, vol. 39 (8-9), pp. 97-101, 1989.
Evans. B.E. et al.. "Design of Nonpeptidal ligands for a Peptide Receptor: Cholecystokinin Antagonists," *J. Med. Chem.* 30:1229-1239 (1987).
Fischer, S., et al., "Uptake, release and metabolism of docosahexaenoic acid (DHA, C22,6w3) in human platelets and neutrophils", *Biochem, Biophys. Res. Commun.*, vol. 120, pp. 907-918, 1984.
Fletcher, M.D. and M.G. Campbell, "Partially Modified Retro-Inverso Peptides: Development, Synthesis, and Conformational Behavior,"*Chem. Rev.*, 98:763-795, (1998).
Fored, C M., et al., "Acetaminophen, aspirin, and chronic renal failure", *N. Engl. J. Med.*, vol. 345, pp. 1801-1808, 2001.
Freeman, S.D. et al., "Characterization of LPS-induced lung inflammation in *cftr* mice and the effect of docosahexaenoic acid", *J. Appl. Physiol.*, vol. 92, pp. 2169-2176, 2002.
Ganz, T. et al., "Antimicrobial peptides of phagocytes and epithelia", *Seminars in Hematology*, vol. 34, No. 4, 1997, pp. 343-354.
Garcia-Cardena, G. et al., "Biomechanical activation of vascular endothelium as a determinant of its functional phenotype", *Proc. Nati Acad. Sci. USA*, vol. 98, pp. 4478-4485, 2001.

Garro-Hellon, et al., "Mild and Selective Palladium( 0)-Catalyzed Deallylation of Allylic Amines. Allylamine and Diallylamine as Very Convenient Ammonia Equivalents for the Synthesis of Primary," Amines, *J. Org. Chem.*, 58;6109-6113, (1993).
Greeling. B.J.. et al.. "Fat intake and fatty acid profile in plasma phospholipids and adipose tissue in patients with Crohn's disease, compared with controls", *Am. J. Gasfroenterol.*, vol. 94, pp. 410-417, 1999.
George, H.J. et al., "Expression purification and characterization of recombinant human inductible prostaglandin G/H synthase from baculovirus-infected insect cells", *Protein Expres. Purif.* 1996, pp. 19-26.
Gilroy, D W. et al. "Inducible cyclooxygenase may have anti-inflammatory properties", *Nature Med.*, vol. 5, pp. 698-701, 1999.
GISSI-Preventive Investigators, "Dietary supplementation with n-3 polyunsaturated fatty acids and vitamin E after myocardial infarction: results of the GISSI-Prevenzione trial", *Lancet*, vol. 354, pp. 447-455, 1999.
Golebiowski, A. and J. Jurczak, "Alpha-Amino- Beta-Hydroxy Acids in the Total Synthesis of Amino Sugars," *Synlett*, pp. 241-245, (Apr. 1993).
Gronert, K , et al , "Transcellular regulation of eicosanoid biosynthesis", *Eicosanoid Protocols* 1999, pp. 119-144.
Gullier, et al., "Linkers and Cleavage Strategies in Solid-Phase Organic Synthesis and Combinatorial Chemistry, " *Chem. Rev.*, 100:2091-2157, (2000).
Gum, P.A., et al., "Aspirin use and all-cause mortality among patients being evaluated for known or suspected coronary artery disease: a propensity", *J.A.M.A.* vol. 286. pp. 1187-1194, 2001.
Gunstone, F.O., et al., "*The Lipid Handbook*", 2nd ed., Chapman & Hall. London. 551 pgs., 1994.
Hanessia, S. et al., "Design and Synthesis of Conformationally Constrained Amino Acids as Versatile Scaffolds and Peptide Manners," *Tetrahedron*, 53:12789-12854, (1997) 145-150.
Herschman, H.R., "Recent progress in the cellular and molecular biology of prostaglandin synthesis", *Trends Cardiovasc. Med.* 1998, pp. 145-150.
Hibbein, J.R. "Fish consumption and major depression", *Lancet*, vol. 351, p. 1213, 1998.
Higuchi, R. et al., "Kinetic PCR analysis: real-time monitoring of DNA amplification reactions", *Biotechnology*, vol. 11, 1993, pp. 1026-1030.
Hill, D.J., et al., "Trout thrombocytes contain 12-but not 5-lipoxygenase activity", *Biochim. Biophys. Acta* 1999, pp. 63-70.
Hill, E.M., et al., "Identification and egg hatching activity of monohydroxy fatty acid eicosanoids in the barnacle Balanus balanoides", *Abstract*. 1992. XP002200247.
Hill, E.M., *Proc R. Soc*. London Ser. B., 247 (1318) pp. 41-46, 1992.
Hong, S. et al., "Novel Docosatrienes and 17S-Resolvins Generated from Docosahexaenoic Acid in Murine Brain, Human Blood, and Glial Cells". *J. Biological Chemistry*, vol. 278, No. 17, pp. 14677-14687, 2003.
Hoyng, C.F. and A.D. Patel, "Aldehyde Components for Use in Four-Component Condensation ("4CC") UGI Reaction Peptide Synthesis," *Tetrahedron Lett.*, 21:4795-4798, (1980).
Humphrey, J.M. and A.R. Chamberlin, "Chemical Synthesis of Natural Product Peptides: Coupling Methods for the Incorporation of Noncoded Amino Acids into Peptides," *Chem. Rev.*
Ikeda, et al., "Chiral Allenylboronic Esters as Practical Reagent for Enantioselective Carbon-Carbon Bond formation Facile Synthesis of (-)Ipsenol," *J. Am. Chem. Soc.* 108:483-4486, 1986.
Jenski, L.J., et al., "Docosahexaenoic acid-induced alteration of Thy-1 and CD8 expression on murine splenocytes", *Biochim. Biophys Acta*. 1236, pp. 39-50, 1995.
Karanian, J.W., et al. "Physiological functions of hydroxy-docosahexaenoic acid". *Abstract*, 1993. XP-002200246.
Karanian, J.W., et al., "Inhibitory Effects of n-6 and n-3 Hydroxy Fatty Acids on Thromboxane (U46619)-Induced Smooth Muscle Contraction", *J. of Pharmacology and Experimental Therapeutics*, vol. 270. No. 3, pp. 1105-1109 (1994) XP009087752.
Kato. T., et al., "Production of Hydroxy Unsaturated Fatty Acids Using Crude Lipoxygenase Obtained from Infected Rice Plants", *Bull. Chem. Soc., Jpn.*, vol. 69, pp. 1663-1666, 1996. XP002200251.

(56) References Cited

OTHER PUBLICATIONS

Khair-El-Din, et al., "Transcription of the Murine iNOS Gene is Inhibited by Docosahexaenoic Acid, a Major Constituent of Fetal and Neonatal Sera as Well as Fish Oils", *J. Exp. Med.*, vol. 183, pp. 1241-1246. 1996.

Khair-El-Din, T., et al., "Transcription of the murine iNOS gene is inhibited by docosahexaenoic acid, a major constituent of fetal serum and fish oil diets inhibits IFNγ-induced la-expression by murine macrophases in vitro", *J. Immunol.*, vol. 154, pp. 1296-1306, 1995.

Khalfoun, B. et al., "Docosahexaenoic and Eicosapentaenoic Acids Inhibit Human Lymphoproliferative Responses In Vitro but not the Expression of T cells Surface Activation Markers", *Scand. J. Immunology*, 43. pp. 248-256, 1996. XP-0000878923.

Kitajka, K., et al., "The role of n-3 polyunsaturated fatty acids in brain: Modulation of rat brain gene expression by dietary n-3 fatty acids". *Proc. Natl. Acad. Sci.*, USA 99, pp. 2619-2624, 2002.

Knapp, Howard R., et al., "Bactericidal Effects of Polyunsaturated Fatty Acids", *The Journal of Infectious Diseases*, vol. 154, No. 1. 1986, pp. 84-94.

Konig, et al., "Synthesis of N-tert-Alkylglyoxylic Acid Amides," *Synthesis*, pp. 1233-1234, (1993), [in German, English language abstract on 1st page of article.

Lacoviello, et al., "Modulation of Fibrinolytic Response to Venous Occlusion in Humans by a Combination of Low-Dose Aspirin and n-3 PUFAs", *Arteriosclerosis Thrombosis*, vol. 10, pp. 1191-1197, 1992.

Lau, et al., "Effects of Fish Oil Supplementation on Non-Steroidal Anti-Inflammatory Drug (NSAID) Requirement in Patients with Mild Rheumatoid Arthritis—A Double-Blind Placebo Controlled Study", *British Journal of Rheumatology*, vol. 32 (11), pp. 982-989, 1993.

Lee, T.H., et al., "Characterization and biologic properties of 5,12-dihydroxy derivatives of eicosapentaenoic acid, including leukotriene B5 and the double lipoxygenase product", *J. Biol. Chem.* 1984, pp. 2383-2389.

Lee, T.H., et al., "Effects of exogenous arachidonic, eicosapentaenoic, and docosahexaenoic acids on the generation of 5-lipoxygenase pathway products by ionophore-activated human neutrophils", *J. Clin. Invest.*, vol. 74, pp. 1922-1933, 1984.

Levy, B.D., et al., "Lipid mediator class switching during acute inflammation: signals in resolution". *Nature Immunol.*, vol. 2, pp. 612-619, 2001.

Levy, G.N., "Prostaglandin I-I synthases, nonsteriodal anti-inflammatory drugs, and colon cancer", *FASEB J.* 1997, pp. 234-247.

Levy, 0., "Antimicrobial proteins and peptides of blood: templates for novel antimicrobial agents", *Blood*, vol. 96, No. 8., 2000, pp. 2664-2672.

Levy, O. "A neutrophil-derived anti-infective molecule: bactericidal/permeability-increasing protein", *Antimicrobial Agents and Chemotherapy*, vol. 44, No. 11, 2000., pp. 2925-2931.

Libby, .P., Atherosclerosis: the new view, *Sci. Am.*, vol. 286, pp. 46-55, 2002.

Ligo, M., et al., Inhibitory effects of docasahexaenoic acid on colon carcinoma 26 metastasis to the lung, *Br. J. Cancer*, 1997, pp. 650-655.

Lockhart, D.J., et al., "Expression monitoring by hybridization tohigh-density oligonucleotide arrays", *Nature Biotechnology*, vol. 14, No. 13, 1996, 1675-1680.

Loeschke, D. et al., *Dig. Dis. Sci.*, vol. 41, 2087-94, (1996).

Maddox, J.F., et al., "Lipoxin $A_4$ and $B_4$ are potent stimuli for human monocyte migration and adhesion: selective inactivation by dehydrogenation and reduction", *J. Exp. Med.*, vol. 183, pp. 137-146, 1996.

Marcheselli, V.L., et al. "Novel Docosenoids Inhibit Brain Ischemia-Reperfusion-mediated Leukocyte Infiltration and Pro-inflammatory Gene Expression", *J. Biological Chemistry*, vol. 278, No. 44, pp. 43807-43817 2003.

Marchioli, R., et al., "Early protection against sudden death by n-3 polyunsaturated fatty acids after myocardial infaction: time-course analysis of the results of the Gruppo Italiano per lo Studion della Sopravvivenze nell'Infarto Miocardico", *Circulation*, vol. 105, pp. 1897-1903, 2002.

Marchioloi, R. "Dietary supplementation with n-3 polyunsaturated fatty acids and vitamin E after myocardial infarction: results of the GISSI-Prevenzione trial", Lancet 1999. pp. 447-455.

Marcus, A.J., "Platelets: their role in hemostasis, thrombosis, and inflammation", Inflammation: Basic Principles and Clinical Correlates 1999, pp. 77-95.

Martinez, M., et al., "Docosahexaenoic acid—a new therapeutic approach to peroxisomal-disorder patients: Experience with two cases", *Neurology*, vol. 43, p. 1389-1397, 1993.

Marx, et al., "Synthetic Design for Combinatorial Chemistry. Solution and Polymer-Supported Synthesis of Polycyclic Lactams by Intramolecular Cyclization of Azomethane Ylides," *J. Am. Chem. Soc.*, 119:6153-6167, (1997).

Marzo, I., et al., "Biosynthesis of docosahexaenoic acid in human cells: evidence that two different $\Delta^6$-desaturase activities may exist", *Biochem. Biophys. Acta*. 1301. pp. 263-272, 1996.

Mata de Urquiza, A., et al., "Docosahexaenoic acids, a ligand for the retinoid X receptior in mouse brain", Science, vol. 290, pp. 2140-2144, 2000.

McCormick. B.A., et al., "*Salmonella typhimurium* attachment to human intestinal epithelial monolayers: transcellular signaling to subepithelial neurophils", *J. Cell Biology*, vol. 123, No. 4, 1993, pp. 895-907.

McLennan, P., et al., "The cardiovascular protective role of the docosahexaenoic acid", *Eur. J. Pharmacol*, vol. 300, pp. 83-89, 1996.

McMahon, B. et al., "Lipoxins: revelations on resolution", *Trends in Pharmacological Sciences*, vol. 22, pp. 391-395, 2001.

Mehta, et al., "Structure-Activity Relationship of a New Class of Anti-Hepatitis B Virus Agents," *Antimicrobial Agents and Chemotherapy*, 46(12) 4004-4008 (2002).

Miller et al., "Guinea Pig Epidermis Generates Putative Anti-Inflammatory Metabolites from Fish Oil Polyunsaturated Fatty Acids", Lipids, *Chemical Abstract* 24(12) 112:117062, pp. 998-1003, 1989.

Miller, C.C. et al., "Dietary supplementation with ethyl ester concentrates of fish oil (n-3) and borage oil (n-6) polyunsaturated fatty acids induces epidermal generation of local putative anti-inflammatory metabolites", *J. Invest. Dermatol*, vol. 96. pp. 98-103. 1991.

Miller, C.C. et al., "Oxidative metabolism of dihomogammalinolenic acid by guinea pig epidermis: Evidence of generation of anti-inflammatory products", *Prostaglandins*, vol. 35, pp. 917-938, 1988.

Needleman, P., et al., "The discovery and function of COX-2", *J. Rheumatol*. 1997, pp. 6-8.

Nicolaou, et al., "Lipoxins and Related Eicosanoids: Biosynthesis, Biological Properties. and Chemical Synthesis", *Angew. Chem. Ed. Engl*. 30:1100-1116, (1991).

Nicolaou, et al., "Novel IBX-Mediated Process for the Synthesis of Amino Sugars and Libraries Thereof," *Angew. Chem. Int. Ed. Engl.*, 39:2525-2529, (2000).

Node, K., et al., "Anti-inflammatory properties of cytochrome P450 epoxygenase-derived eicosanoids", *Science* 1999, pp. 1276-1279.

Noyori, R. (Ed.), "Enantioselective Addition of Organometallic Reagents to Carbonyl Compounds: Chirality Transfer, Multiplication, and Amplification," Chapter 5 in *Asymmetrical Catalysts in Organic Synthesis*, New York; Wiley & Sons, Inc., pp. 255-297 (1994).

Nugent, William A., "Chiral Lewis Acid Catalysis, Enantioselective Addition of Azide to Meso Epoxides", *J. Am. Chem. Soc.*, 114(7): 2768-2769 (1992).

O'Donnell, Martin J. and J. Falmagne. "The Synthesis of Amino Acids via Organoboranes." *J. Chem. Soc. Chem. Commun..*, No. 17, pp. 1168-1169. (Sep. 1, 1985).

O'Banion, M.K., et al., "cDNA cloning and functional activity of a glucocorticoid-regulated inflammatory cyclooxygenase", *Proc. Natl. Acad. Sci. USA*, vol. 89, pp. 4888-4892, 1992.

Olfson, M., et al., "National trends in the outpatient treatment of depression", *JAMA*, vol. 287. pp. 203-209, 2002.

Palrnantier, R. et al., "Transcellular metabolism of arachidonic acid in platelets and polymorephonuclear leukocytes activated by physi-

(56) References Cited

OTHER PUBLICATIONS ological agonists: enhancement of leukotriene $B_4$ synthesis", *Cell-Cell Interactions in the Release of Inflammatory Mediators*, vol. 314, pp. 73-89, 1991.
Petasis, N.A. and I.A. Zavialov, "The Boronic Acid Mannich Reaction: A New Method for the Synthesis of Geometrically Pure Allylamines." *Tetrahedron Letters*, 34(4):538-586, (1993).
Petasis, N.A. and TA Zavialov, "A New and Practical Synthesis of Alpha Amino Acids from Alkenyl Boronic Acids," *J. Am. Chem. Soc.*, 119(2):445-446, (1997).
Pfaffi, M.W., "A new mathematical model for relative quantification in real-time, RT-PCR" Nucleic Acids Research, vol. 29, No. 9, 2001, pp. 2002-2007.
Poling, J.S., et al., "Docosahexaenoic acid block of neuronal voltage-gated $K^+$. channels: subunit selective antagonism by zinc", *Neuropharmacology*, vol. 35, pp. 969-982. 1996.
Pullarkat, R.K. et al.. "Leukocyte docosahexaenoic acid in juvenile form of ceroid-lipofuscinosis," *Neuropadiatrie*, vol. 9, pp. 127-130, 1978.
Qiu, F.H. et al., "Aspirin-triggered lipoxin $A_4$ and lipoxin $A_4$. up-regulate transcriptional corepressor NAB1 in human neutrophils", *FASEB J.* 1096/fj. 1001-0576fje, vol. 10, 2001.
Rao, et al, "Comparative Pharmacology of Cyclooxygenase Inhibitors on Platelet Function", *Prostaglandins Leukot. Med.*, vol. 18 (1), pp. 119-131, 1985.
Rapp, J.H. et al., "Dietary eicosapentaenoic acid and docosahexaenoic acid from fish oil", *Arteriosclerosis and Thrombosis*, vol. 11, pp. 903-911, 1991.
Reddy, T.D., et al., "Change in content, incorporation and lipoxygenation of docosahexaenoic acid in retina and retinal pigment epithelium in canine ceroid lipofuscinosis", *Neuroscience Lett.*, vol. 59,1:67-72, 1985.
Reich, E.F. et al., "Formation of novel D-ring and E-ring isoprostane-like compounds ($D_4/E_4$-neuroprostanes) in vivo from docosahexaenoic acid". *Biochemistry*, vol. 39, pp. 2376-2383, 2000.
Reynaud et al., *Analytical Biochemistry* (1993), 214(1), p. 165-170, (CA 119:265901).
Ridker, P.M., et al., "Inflammation, aspirin, and the risk of cardiovascular disease in apparently healthy men", *N. Engl. J. Med.* 1997, pp. 973-979.
Rodriguez and Spur, "Total synthesis of aspirin-triggered 15-epi-lipoxin A4" *Tetrahedron Lett.*, 42: 6057-6060, 2001.
Rowlinson, S.W., et al., "Spatial requirements for 15-(R)-hydroxy-5Z,8Z,11Z,13E-eicosatetraenoic acid synthesis withing the cyclooxygenase active site of murine COX-2". *J. Biol. Chem.*, vol. 275, pp. 6586-6591, 2000.
Rosenberg. H. et al., "Fish—food to calm the heart", *N. Engl. J. Med.*, vol. 346, pp. 1102-1103, 2002.
Rowley, A.F., et al., "Haemostasis in fish—an evolutionary perspective", *Throm. Haemost.*, vol. 77 pp. 227-233, 1997.
Ruettinger, R.T., et al.. "Epoxidation of unsaturated fatty acids by a soluble cytochrome P-45-dependent system from *Bacillus megaterium*", *J. Biol. Chem.* 1981, "s. 5728-5734.
Salem. N., et al., "Arachidonic and docosahexaenoic acids are biosynthesized from their 18-carbon precursors in human infants", *Proc. Natl. Acad. Sci. USA*, vol. 93, pp. 49-54, 1996.
Samuelsson, B., "From studies of biochemical mechanisms to novel biological mediators: prostaglandin endoperoxides, thromboxanes, and leukotrienes", in *Les Prix Nobel*. pp. 165-174, 1982.
Samuelsson, B., et al., "Leukotrienes and lipoxins structure, biosynthesis, and biological effects", *Science*, vol. 237, pp. 1171-1176, 1987.
Sawazaki, S., et al., "Lipoxygenation of docosahexaenoic acid by the rate pineal body", *J. Neurochem.*, vol. 62, pp. 2437-2447, 1994.
Schmedtje, Jr., J.F., et al., "Hypoxia Induces Cyclooxyenase-2 via the NF-κB p65 Transcription Factor in Human Vascular Endothelial Cells", *J. Biolog.Chem.*, vol. 272, No. 1, pp. 601-608, 1997.
Serhan et al., "Resolvins, Docosatrienes, and Neuroprotectins, Novel Omega-3-Derived Mediators, and their Aspirin-Triggered EndogenousEpimers: An Overview of Their Protective Roles in Catabasis", *Prostaglandins Other Lipid Mediat*. 5543, 1-18, 2004.
Serhan, "A Search for Endogenous Mechanisms of Anti-Inflammation Uncovers Novel Chemical Mediators: Missing Links to Resolution", *Histochem. Cell Biol*. 122(4): 305-321, 2004.
Serhan, "Novel Eicosanoid and Docosanoid Mediators: Resolvins. Docosatrienes. and Neuroprotectins", *Curr Opin Clin Nutr Metab Care*, 8(2): 1-7, 2005.
Serhan, "Novel Omega-3-Derived Local Mediators in Anti-Inflammation and Resolution". *Pharmacol Ther*. 105(1): 7-21, 2005.
Serhan, "Resolvins, Docosatnenes, and Neuroprotectins, Novel Omega-3-Derived Mediators, and their Endogenous Aspirin-Triggered Epimers", *Lipids*, 73:155-172, 2004.
Serhan, C. N. et al., "Novel Functional Sets of Lipid-derived Mediators with Antiinflammatory Actions Generated from Omega-3 Fatty Acids via Cyclooxygenase 2-Nonsteroidal Antiinflammatory Drugs and Transcellular Processing", *Journal of Medicine*, Tokyo Japan, vol. 192, No, 8, Oct. 16, 2000, pp. 1197-1204, XP002267884. ISSN: 0022-1007.
Serhan, C.N. et al., "Design of lipoxin A4 stable analogs that block transmigration and adhesion of human neutrophils", *Biochemistry* 1995, pp. 14609-14615.
Serhan, C.N. et al., "Resolvins: a family of bioactive products of omega-3 fatty acids transformation circuits initiated by aspirin treatment that counter proinflammation signals". *J. Exp. Med*. , vol. 196. No. 8, pp. 1025-1037, 2002.
Serhan, C.N. et al., "Unorthodox routes to prostanoid formation: new twists in cyclooxygenase- initiated pathways", *J. Clin. Invest*. vol. 107, pp. 1481-1489, 2001.
Serhan, C.N., et al., "Nomenclature of lipoxins and related compounds derived from arachidonic acid and eicosapentaenoic acid", *Prostaglandins* 1987, pp. 201-204.
Serhan, C.N., et al., "Novel functional sets of lipid-derived mediators with antiinflammatory actions generated from omega-3 fatty acids via cycloxygenase 2-nonsterioidal antiinflammatory drugs and transcellular processing", *J. Exp. Med.*, vol. 192, pp. 1197-1204, 2000.
Serhan, et al., "Novel Pathways and Endogenous Mediators in Anti-Inflammation and Resolution", *Chem Immunol Allergy*, 83: 115-145, 2003.
Serhan, et al., "Resolvins, Docosatrienes, and Neuroprotectins, Novel Omega-3-Derived Mediators, and Their Aspirin-Triggered Endogenous Epimers", *Lipids* 39, 1125-1132, 2004.
Seman, et al., Novel Endogenous Small Molecules as the Checkpoint Controllers in Inflammation and Resolution: Entree for Resoleomics' *Rheum Dis Clin North Am*. 30(1): 69-95, 2004.
Sethi, S., et al., "Inhibition of phagocyte-endothelium interactions by oxidized fatty acid's: A natural anti-flammatory mechanism?", J. Lab Dim Med. 1996, pp. 27-38.
Shimizu, T., et al., "Enzyme with dual lipoxygenase activities catalyzes leukotriene A4 synthesis from arachidonic acid", *Proc. Natl. Acad. Sci. USA*, vol. 81, pp. 689-693. 1984.
Shinmura, K., et al., "Cyclooxygenase-2 mediates the cardioprotective effects of the late phase of ischemic preconditioning in conscious rabbits", *Proc. Natl. Acad. Sci. USA*, vol. 97, pp. 10197-10202, 2000.
Simopoulos, A.P. Workshop on the essentiality of an recommended dietary intakes for omega-6 and omega-3 fatty acids, *J. Am. Coll. Nutr*. 1999, pp. 487-489.
Srivastava, K.C., "Docosahexaenoic acid (C22:6w3) and linoleic acid are anti-aggregatory, and alter arachidonic acid metabolism in human platelets", *Prostaglandins Leukot. Med.*, vol. 17, pp. 319-327, 1985.
Taylor, C.T., et al., "Critical role of cAMP response element binding protein expression in hypoxia-elicited induction of epithelial tumor necrosis factor-a", J. Biol. Chem., vol. 274, No. 27, 1999, 19447-19454.
Terano, Takeshi, *Chemical Abstract* 107:22439, pp. 63-71, 1987.
Terano, Takeshi, et al., "Eicosapentaenoic acid and docosahexaenoic acid inhibit vascular smooth muscle cell proliferation by inhibiting phosphorylation of Cdk2-cyclinE complex", *Biochem. Biophys. Res. Commun.*, vol. 254, pp. 502-506.
Thompson, L.A. and J.A. Ellman, "Synthesis and Applications of Small Molecule Libraries," *Chem. Rev*. 96:555-6000 (1996).

(56) References Cited

OTHER PUBLICATIONS

Tou, J., "Acylation of docosahexaenoic acid into phospholipids by intact human neutrophils", *Lipids*, vol. 21, pp. 324-327, 1986.

Van Dyke, et al., "Resolution of Inflammation: A New Paradigm for the Pathogenesis of Periodontal Diseases", *J. Dent. Res.* 82(2)7 82-90, 2003.

Levy, Bruce D., et al., "Protectin D1 is Generated in Asthma and Dampens Airway Inflammation and Hyperresponsiveness.," *The Journal of Immunology*, 2007, 178: 496-502.

Van Rollins, M. et al., "Autooxidation of docosahexaenoic acid analysis of ten isomers of hydroxydocosahexaenoate", *J. Lipid Res.*, vol. 25, pp. 507-517, 1984.

Van Rollins, M., et al., "Oxidation of docosahexaenoic acid by rat liver microsomes", *J. Biol. Chem.*, vol. 259, pp. 5776-5783, 1984.

Vane, J.R., et al., "Therapeutic Roles of Selective COX-2 Inhibitors", *William Harvey Press*, London, 2001.

W.E.M. Lands, "Proceedings of the AOCS Short Course on Polyunsaturated Fatty Acids and Eicosanoids", *American Oil Chemists Society*, 1987.

Waki, M. and J. Meienhofer, "Peptide Synthesis Using the Four-Component Condensation (Ugi Reaction)," *J. Am. Chem. Soc.*, 99:6075-6082, (1977).

Weersink, A., et al., "Human granulocytes express a 550-kDa lipoplysaccharide binding protein on the cell surface that is identical to the bactericidal/permeability-increasing protein", *J. Immunology*, vol. 150, No. 1. 1993, pp. 253-263.

Weiss, J. et al., "Purification and characterization of a potent bactericidal and membrane active protein from the granules of human ppolymorphonuclear leukocytes", *J. Biol. Chem.* vol. 253, No. 8, 1978, pp. 2664-2672.

Weissmann, G., "Aspirin", *Sci. Am.* 1991, pp. 84-90.

Whelan, J., et al., "The unique characteristics of the purified 5-lipoxygenase from potato tubers and the proposed mechanism of formation of leukotrienes and lipoxins", *Biological •Oxidation Systems*, vol. 2 pp. 765-778, 1990.

Xiao, G. et al., "Analysis of hydroperoxide-induced tyrosyl radicals and lipoxygenase activity in aspirin-treated human prostaglandin H synthase-2", *Biochemistry* 1997, pp. 1836-1845.

Yamane, M., et al., "Docosahexaenoic/arachidonic acid omega-hydroxylation system and differentiation in the human clonic adenocarcinoma cell line, Caco-2", *Cancer Letters*, vol. 122, pp. 51-59, 1998. XP002200245.

Yamomoto, Y. and N. Asao, "Selective Reactions Using Allylic Metals". *Chem. Rev.*, 93:2207-2293, (1993).

Yergey, J.A. et al., "High-performance liquid chromatography/thermospray mass spectrometry of eicosanoids and novel oxygenated metabolites of docosahexaenoic acid", *Anal. Chem.*, vol. 58, pp. 1344-1348, 1986.

Yokomizo, T., et al., "A G-protein-coupled receptor for leukotriene B4 that mediates chemotaxis", *Nature* 1997, pp. 620-624.

Zeldin, D.C. "Epoxygenase pathways of arachidonic acid metabolism", *J. Biol. Chem.*, vol. 276, pp. 36059-36062, 2001.

Ziboth, V.A., et al.. "Inhibition of sheep vesicular gland oxygenase by unsaturated fatty acids from skin of essential fatty acid deficient rats", *Prostaglandins*, vol. 5, pp. 233-240, 1974.

Ziboth, V.A., et al.. "Metabolism of polyunsaturated fatty acids by skin epidermal enzymes: generation of antiinflammatory and antiproliferative metabolities", *Am. J. Clin. Nutr.*, vol. 71 (Suppl.), pp. 361S-366S, 2000.

Chemical Abstracts online citation, AN:2004:143088, retrieved Aug. 15, 2007 from STN, Columbus, OH.

Hong, et al., "Rainbow trout (*Oncorhynchus mykiss*) brain cells biosynthesize novel docasahexaenoic acid-derived resolvins and protectins—mediator liidomic analysis", *Prostaglandins & Other Lipid Mediators*, Elsevier, vol. 78, No. 1-4, Jun. 13, 2005, 107-116. XP005174168.

Serhan, Charles N. et al., "Anti-Inflammatory Actions of Neuroprotectin DI/ProtectinD1 and it's Natural Stereoisomers: Assignments of Dihydroxy-Containing Docosatrienes", Journal of Immunology. 176(3). 1848-1859 Coden: JO1MA3: ISSN 0022-1767, Feb. 1, 2006. XP002429095.

PCT/US2006/038326 International Search Report dated Apr. 23, 2007.

PCT/US2006/000306 International Search Report dated Jul. 14, 2006.

PCT/US2003/25336 International Search Report dated Feb. 16, 2004.

PCT/US2001/05196 International Search Report dated Jul. 19, 2002.

EP 06 02 2386 European Search Report dated Oct. 5, 2007.

PCT/US2005/12552 International Search Report dated Aug. 24, 2005.

PCT/US2006/011222 International Search Report dated Oct. 5, 2007.

PCT/US2005/009056 internattonal Search Report dated Nov. 16, 2005.

\* cited by examiner

TREATMENT AND PREVENTION OF BONE LOSS USING RESOLVINS

RELATED APPLICATIONS

The present application claims priority from Provisional Application No. 60/738,328 filed on Nov. 18, 2005 and entitled "Treatment and Prevention of Bone Loss Using Resolvins". The Provisional Application is incorporated herein by reference in its entirety.

GOVERNMENT SUPPORT

This invention was made with Government Support under Contract No. DE16191 awarded by the National Institutes of Health. The Government has certain rights in the invention.

BACKGROUND OF THE INVENTION

Periodontal disease, ranging from gingivitis to more severe forms of periodontitis, remains a significant health problem and is a major cause of tooth loss in adults both in the United States and throughout the world (E. Reich and K. Hiller, Comm. Dent. Oral Epidem., 1993, 21: 379; J. Angelillo et al., Comm. Dent. Oral Epidem., 1996, 24: 336; H. Murray et al., Int. Dent. J., 1997, 47: 3-8; R. C Oliver et al., J. Periodontol., 1998, 69: 269-278; G. Ong, Int. Dental J., 1998, 48: 233-238; I. Haddad et al., Dental J., 1999, 49: 343-346; E. F. Corbet et al., Periodontology, 2000, 29: 122-152; A. Sheiham et al., Periodontology, 2000, 29: 104-121; I. Chestnutt et al., J. Dentist., 2000, 28: 295-297; U. M. Irfan et al., J. Int. Acad. Periodontol., 2001, 3: 14-21). It is estimated that different types of periodontal disease affect 15-35% of the U.S. population, which translates into tens of millions of patients (J. M. Albandar et al., J. Peridontol., 1999, 70: 13-29) and costs billions of dollars a year. Furthermore, periodontal disease has implications beyond the deleterious effects on oral tissues and structural integrity, and represents a potential risk factor for increased morbidity and mortality for several systemic conditions including cardiovascular diseases, pregnancy complications and diabetes (R. C. Page et al., Ann. Periodontol., 1998, 3: 108-120; R. I. Garcia et al., Ann. Periodontol., 1998, 3: 339-349).

Periodontitis is an infectious disease in which an inflammatory process is stimulated by the presence of plaque that may lead to loss of clinical attachment and alveolar bone. The most common form of periodontal disease is observed in adults and shows chronic progression (I. Brook, Gen. Dent., 203, 51: 424-428). The progression of periodontal disease relies on persistence of chronicity of the host response. Out of the hundreds of bacterial species present in the oral cavity, only a small number are involved in the etiology of periodontal disease (S. S. Socransky and A. D. Haffajee, Periodontal., 2002, 28: 12-55). The biofilm may contain bacteria, such as *Porphyromonas gingivalis, Bacteroides forsythus*, and *Treponema denticola*, the presence of which is strikingly related to clinical features of periodontal disease, in particular the pocket depth and bleeding on probing (S. S. Socransky et al., J. Clin. Periodontol., 1998, 25: 134-144). Some of these pathogenic organisms can invade periodontal tissues, dentinal tubules, as well as other areas of the oral cavity. Conventional periodontal therapy has emphasized mechanical removal of soft and hard accretions of bacteria from the root surface via use of dental instruments placed into the gingival crevice to mechanically shear the accretions from the tooth structure. However, scaling and root planning is often only partially effective in the removal of these accretions. Moreover, even in the case of easily accessible areas, the removal is transient and the bacteria re-colonize the root surface.

When virulent bacteria begin to flourish in the periodontal region, they release toxic and pathogenic products under the gum-line that induce an inflammatory response and can cause a chronic infection. As the bacterial toxins dissolve the alveolar bone, the gums and bone can recede together, exposing the roots of the teeth. In other instances, the bone can recede but the gums remain puffy and form a wall around the pockets of debris that have replaced the lost bone. In both circumstances, the roots of the teeth become exposed to either air or to irritating bacterial toxins, both of which can cause spontaneous pain or tooth sensitivities to cold, hot or sweet or sour food. Although the damage caused by bone loss is usually permanent, early periodontitis can be arrested with proper home oral hygiene and the risk of tooth loss is minimal. As bone loss progresses, more aggressive treatment must be performed to keep the teeth clean. If bone loss continues and the tooth support is compromised, the teeth become mobile and eventually are lost or need to be extracted.

Current treatment of periodontal diseases involve primarily the use of compositions containing antimicrobial compounds or various non-steroidal anti-inflammatory agents (NSAIDs). Systemic antibiotics have been used in the periodontal therapy (R. J. Genco, J. Periodontal., 1981, 52: 545-558). However, systemic delivery (e.g., oral or intramuscular) typically does not provide a sufficient concentration of antibiotics over an extended period of time to the gingival crevice area. In advanced cases of periodontal disease, surgical intervention to eliminate the periodontal pocket and recontour the bone may be performed. Splinting of loose teeth and selective reshaping of tooth surfaces to eliminate traumatic occlusion may be necessary. Despite these known treatments, there remains a need for novel, improved methods for preventing and treating periodontal diseases. In particular, methods for preventing and treating periodontitis-related bone loss are highly desirable.

SUMMARY OF THE INVENTION

The present invention relates to new systems and strategies for the non-invasive treatment of bone conditions associated with bone loss. One aspect of the present invention encompasses the recognition that topical administration of Resolvin E1 unexpectedly prevents bone loss in *P. gingivalis*-induced periodontitis in a rabbit model. In particular, the present Applicants have shown that resolvin-treated rabbits exhibits distinctly healthier soft tissues than rabbits in a control group. Furthermore, soft tissue pocket depth, hard tissue crestal distance, hard tissue-infrabony pocket depth and tooth mobility measurements in the resolvin-treated groups were observed to be lower than in the control group suggesting that Resolvin E1 was assisting in deposition of bone, i.e., in bone growth.

Accordingly, methods and compositions are provided herein for inducing or promoting bone growth and/or for reducing or preventing bone resorption in a vertebrate subject, including humans and animals.

More specifically, in one aspect, the present invention provides a method of treating a bone condition in a vertebrate subject, comprising a step of administering to the subject an effective amount of at least one resolvin. In certain embodiments, the bone condition is associated with bone loss. The bone condition may be selected from the group consisting of periodontal disease (e.g., gingivitis or periodontitis), bone fracture, bone deficiency, metastatic bone disease, osteoarthritis, and osteolytic bone disease.

In certain embodiments, the method results in one or more of: prevention of bone deterioration, prevention of bone degradation, prevention of bone degeneration, prevention of loss of bone mass, prevention of loss of bone density, stabilization of bone deterioration, stabilization of bone degradation, stabilization of bone degeneration, stabilization of loss of bone mass, stabilization of loss of bone density, decrease of bone deterioration, decrease of bone degradation, decrease of bone degeneration, decrease of loss of bone mass, decrease of loss of bone density, increase of bone mass, increase of bone density, and combinations thereof.

In certain embodiments, the resolvin is administered topically, for example to the subject's oral cavity. In other embodiments, the resolvin is administered enterally, for example orally.

Resolvins administered according to the present invention may be selected from the group consisting of members of the Resolvin E series, members of the Resolvin D series, and combinations thereof. For example, resolvins may be selected from the group consisting of di-hydroxy members of the Resolvin E series, di-hydroxy members of the Resolvin D series, tri-hydroxy members of the Resolvin E series, tri-hydroxy members of the Resolvin D series, and combinations thereof. In certain embodiments, the resolvin administered comprises Resolvin E1.

In certain embodiments, the method further comprises a step of administering to the subject an effective amount of a therapeutic agent that promotes bone growth or inhibits bone resorption. The steps of administering the resolvin and administering the therapeutic agent that promotes bone growth or inhibits bone resorption may be performed sequentially or simultaneously.

In certain embodiments, the therapeutic agent that promotes bone growth or inhibits bone resorption is selected from the group consisting of bone morphogenetic factors, anti-resorptive agents, osteogenic factors, cartilage-derived morphogenetic proteins, growth hormones, estrogens, bisphosphonates, statins, differentiating factors, and combinations thereof.

In another aspect, the present invention provides a pharmaceutical composition comprising at least one resolvin, at least one therapeutic agent that promotes bone growth or inhibits bone resorption, and at least one pharmaceutically acceptable carrier or excipient.

Resolvins present in pharmaceutical compositions of the present invention may be selected from the group consisting of members of the Resolvin E series, members of the Resolvin D series, and combinations thereof. For example, resolvins may be selected from the group consisting of di-hydroxy members of the Resolvin E series, di-hydroxy members of the Resolvin D series, tri-hydroxy members of the Resolvin E series, tri-hydroxy members of the Resolvin D series, and combinations thereof. In certain embodiments, the resolvin present in an inventive pharmaceutical composition comprises Resolvin E1.

In certain embodiments, the therapeutic agent that promotes bone growth or inhibits bone resorption present in pharmaceutical compositions of the present invention may be selected from the group consisting of bone morphogenetic factors, anti-resorptive agents, osteogenic factors, cartilage-derived morphogenetic proteins, growth hormones, estrogens, bisphosphonates, statins, differentiating factors, and combinations thereof.

A pharmaceutical composition of the present invention may be formulated to be administered enterally, for example orally, or topically. In certain embodiments, a pharmaceutical composition is formulated to be topically administered to a subject that is susceptible to or is suffering from a bone condition associated with bone loss, for example, periodontal disease (e.g., gingivitis or periodontitis), bone fracture, bone deficiency, metastatic bone disease, osteoarthritis, and osteolytic bone disease. For example, a pharmaceutical composition may be formulated to be administered to the subject's oral cavity, for example as a solution, suspension, dispersion, ointment, cream, gel, toothpaste, tooth powder, lozenge, salve, chewing gum, aerosol, mouth spray, pastille, sachet, mouthwash, toothpick, tablet, capsule, or dental floss.

In certain embodiments, a pharmaceutical composition further comprises at least one additional therapeutic agent selected from the group consisting of analgesics, anesthetics, antimicrobial agents, antibacterial agents, antiviral agents, antifungal agents, antibiotics, anti-inflammatory agents, antioxidants, antiseptic agents, immunostimulating agents, and combinations thereof.

Administration of pharmaceutical compositions of the present invention results in one or more of prevention of bone deterioration, prevention of bone degradation, prevention of bone degeneration, prevention of loss of bone mass, prevention of loss of bone density, stabilization of bone deterioration, stabilization of bone degradation, stabilization of bone degeneration, stabilization of loss of bone mass, stabilization of loss of bone density, decrease of bone deterioration, decrease of bone degradation, decrease of bone degeneration, decrease of loss of bone mass, decrease of loss of bone density, increase of bone mass, increase of bone density, and combinations thereof.

In another aspect, the present invention provides a kit for treating a bone condition associated with bone loss in a vertebrate subject, the kit comprising at least one resolvin and at least one therapeutic agent that promotes bone growth or inhibits bone resorption. Resolvins and therapeutic agents of these kits may be as described above for the pharmaceutical compositions. Similarly, bone conditions that can be treating using the kit are as described above.

In certain embodiments, the kit further comprises instructions for administering the resolvin and therapeutic agent that promotes bone growth or inhibits bone resorption to the subject (human or animal), preferably according to a method of the present invention. Administration (e.g., topical or enteral administration) of the resolvin and therapeutic agent may be performed sequentially or simultaneously.

Using an inventive kit for treating a bone condition associated with bone loss preferably results in one or more of: prevention of bone deterioration, prevention of bone degradation, prevention of bone degeneration, prevention of loss of bone mass, prevention of loss of bone density, stabilization of bone deterioration, stabilization of bone degradation, stabilization of bone degeneration, stabilization of loss of bone mass, stabilization of loss of bone density, decrease of bone deterioration, decrease of bone degradation, decrease of bone degeneration, decrease of loss of bone mass, decrease of loss of bone density, increase of bone mass, increase of bone density, and combinations thereof.

These and other objects, advantages and features of the present invention will become apparent to those of ordinary skill in the art having read the following detailed description.

*lis*+vehicle alone (middle column), ligature+*P. gingivalis*+Resolvin E1 (RvE1) in vehicle (last column).

Figure 3:
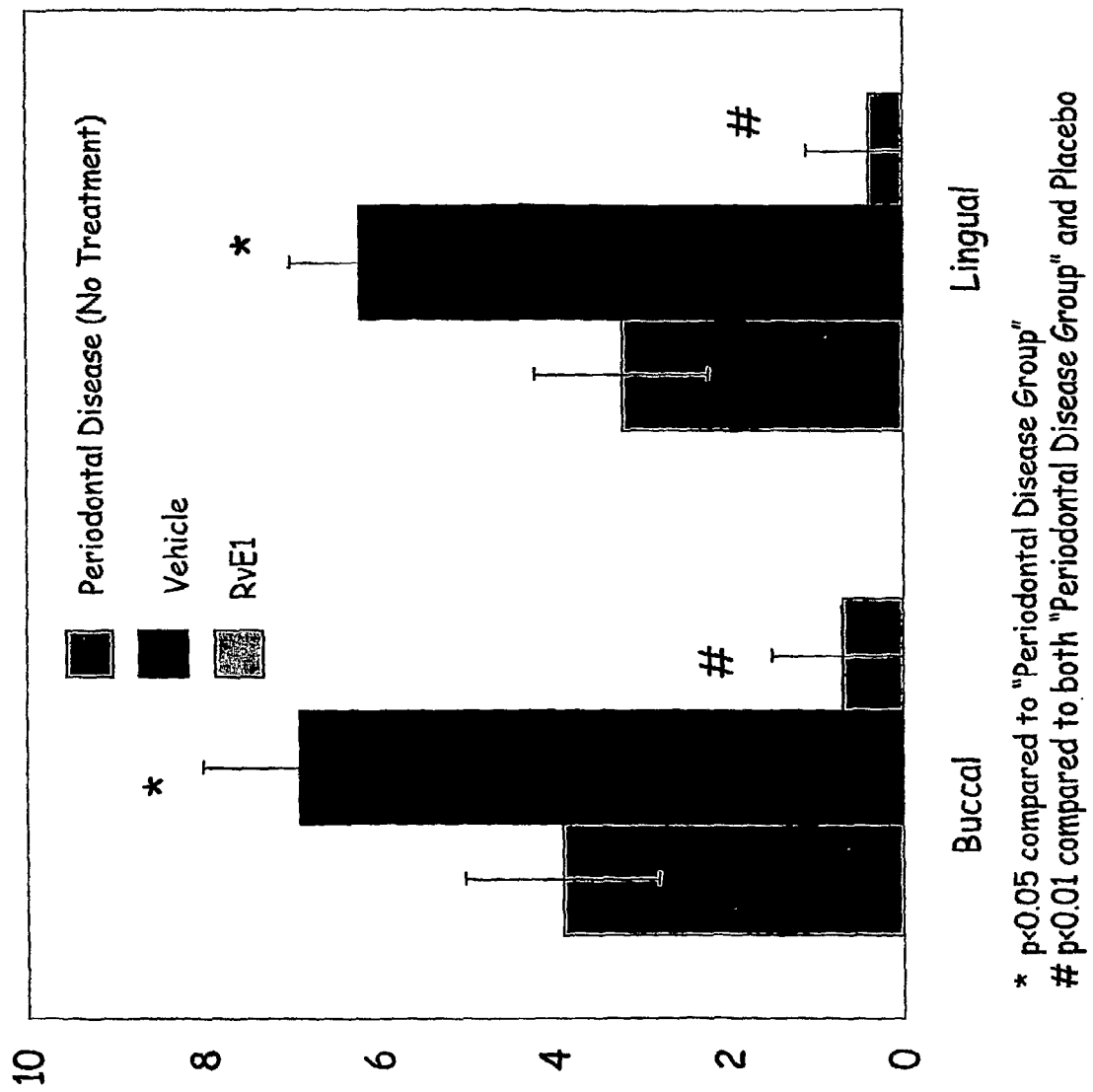

FIG. 3 presents, on a graph, the results of a quantitative analysis of soft tissue-pocket depth measurements as a function of localization in the oral cavity (i.e., buccal and lingual) and as a function of treatment received by the different animal groups (i.e., ligature+*P. gingivalis* or "Periodontal disease (No Treatment)"; ligature+*P. gingivalis*+vehicle alone or "Vehicle"; and ligature+*P. gingivalis*+Resolvin E1 in vehicle or "RvE1").

Figure 4:
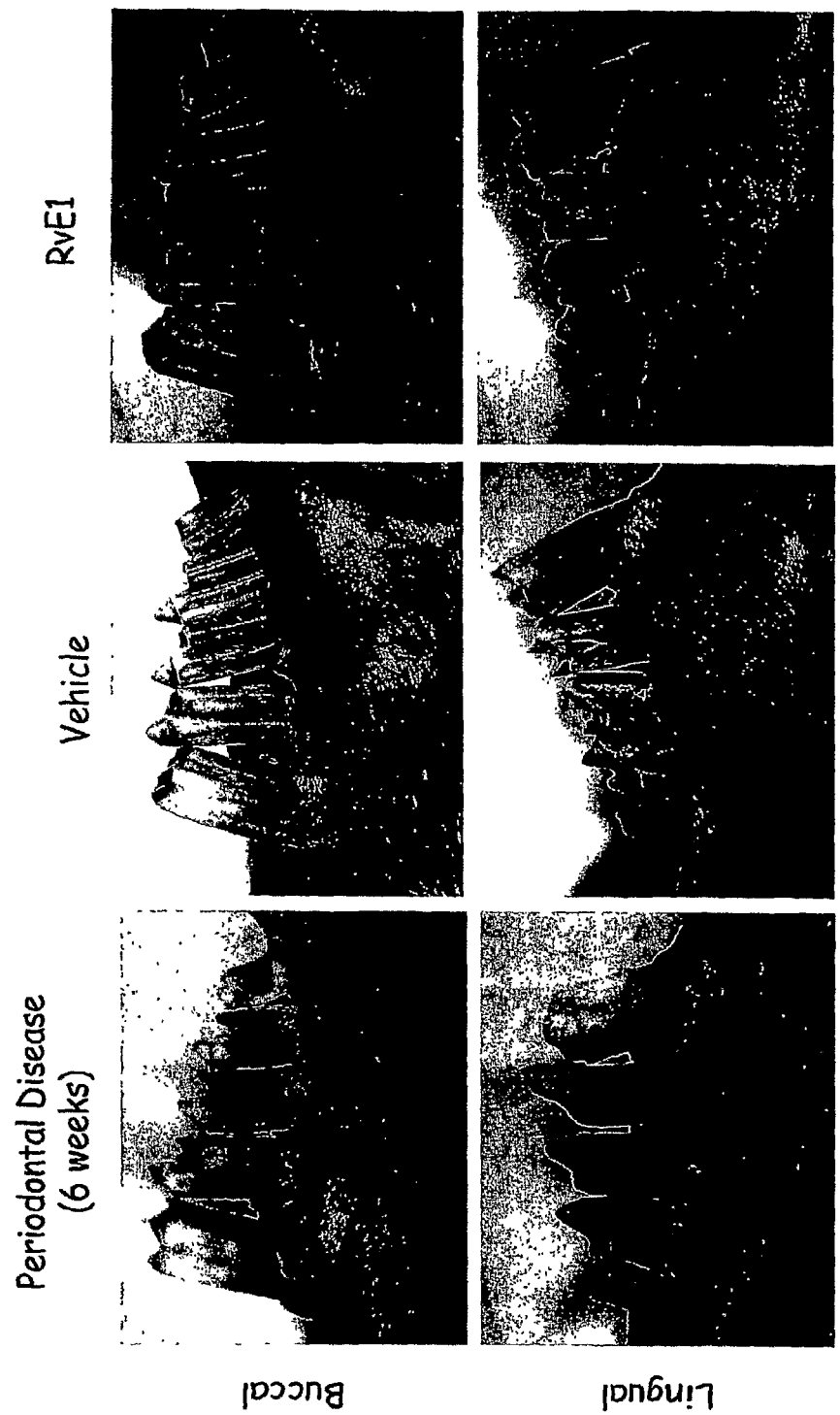

FIG. 4 presents pictures of the buccal and lingual mandibles of rabbits after defleshing of jaws to directly examine the bone. The rabbits were treated by ligature+*P. gingivalis* (first column), ligature+*P. gingivalis*+vehicle alone (middle column), ligature+*P. gingivalis*+Resolvin E1 (RvE1) in vehicle (last column).

Figure 5:
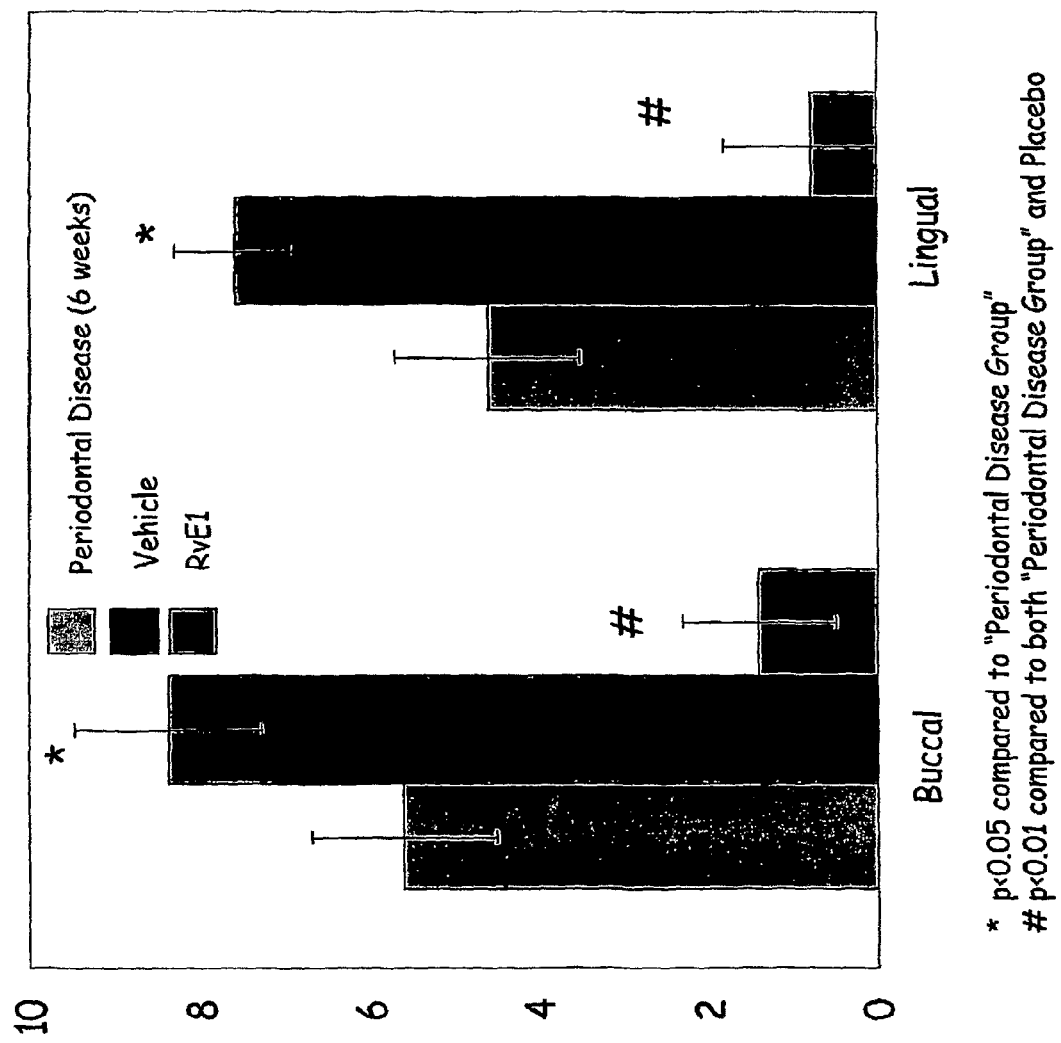

FIG. 5 presents, on a graph, the results of a quantitative analysis of hard tissue-crestal distance measurements as a function of localization in the oral cavity (i.e., buccal and lingual) and as a function of treatment received by the different animal groups (i.e., ligature+*P. gingivalis* or "Periodontal disease (No Treatment)"; ligature+*P. gingivalis*+vehicle alone or "Vehicle"; and ligature+*P. gingivalis*+Resolvin E1 in vehicle or "RvE1").

Figure 6:
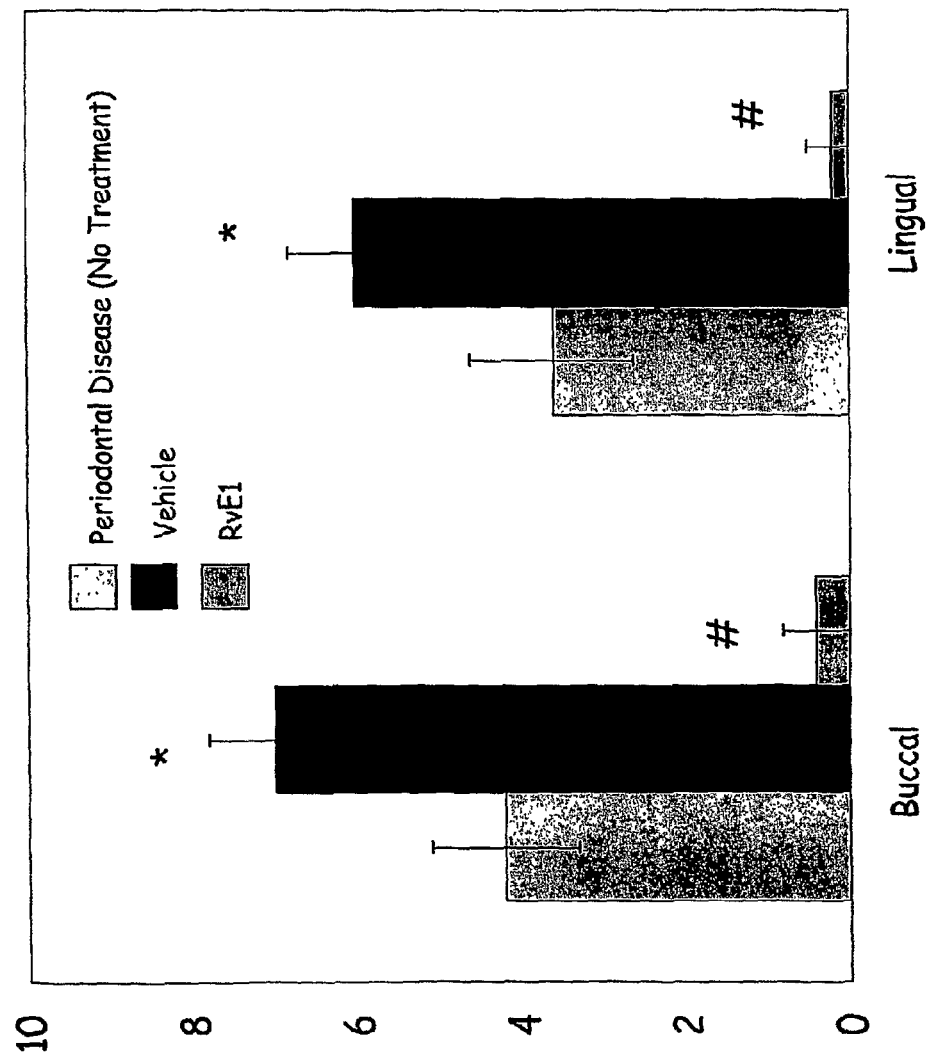

FIG. 6 presents, on a graph, the results of a quantitative analysis of hard tissue-infrabony pocket depth measurements as a function of localization in the oral cavity (i.e., buccal and lingual) and as a function of treatment received by the different animal groups (i.e., ligature+*P. gingivalis* or "Periodontal disease"; ligature+*P. gingivalis*+vehicle alone or "Vehicle"; and ligature+*P. gingivalis*+Resolvin E1 in vehicle or "RvE1").

Figure 7:
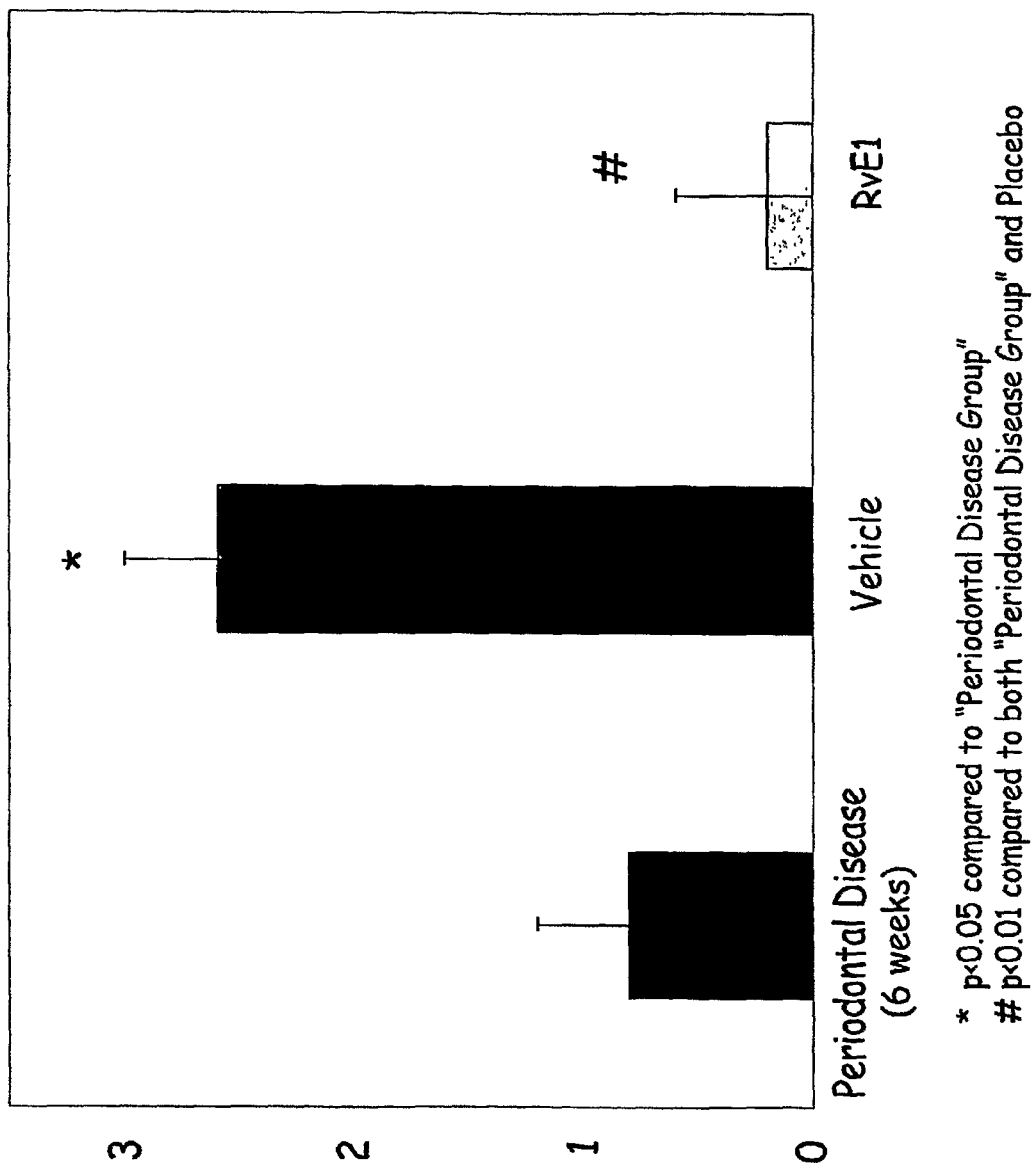

FIG. 7 presents, on a graph, the results of a quantitative analysis of tooth mobility as a function of treatment received by the different animal groups (i.e., ligature+*P. gingivalis* or "Periodontal disease"; ligature+*P. gingivalis*+vehicle alone or "Vehicle"; and ligature+*P. gingivalis*+Resolvin E1 in vehicle or "RvE1").

DEFINITIONS

Throughout the specification, several terms are employed that are defined in the following paragraphs.

The terms "individual" and "subject" are used herein interchangeably. They refer to a higher vertebrate, preferably a human or another mammal (e.g., a mouse, rat, rabbit, monkey, dog, cat, pig, cow, horse, and the like) that can suffer from a disease state or condition for which administration of a resolvin is beneficial but may or may not have the disease state or condition. In many embodiments, the subject is suffering from or is susceptible to (i.e., exhibits a high or higher risk of developing) a bone condition, for example, a bone condition associated with bone loss. In certain embodiments, the subject is a human being. The terms do not denote a particular age, and thus encompass adults, children and newborns.

As used herein, the term "bone condition" includes any condition where it is desirable to increase, improve or promote bone mass and/or bone density and/or prevent, inhibit or reduce the loss of bone mass and/or bone density. The term "bone condition" encompasses any condition that increases osteoclast number, increases osteoclast activity, increases bone resorption, increases marrow fibrosis, or alters the calcium content of bone.

As used herein, the term "bone loss" refers to any situation in which skeletal mass, substance or matrix or any component of the skeleton, such as calcium and phosphate, is decreased or the bone or the tooth is lost, damaged, or weakened such as in terms of its ability to resist being broken. The term "bone loss" also encompasses any situation characterized by bone deterioration, bone degradation, bone degeneration, loss of bone mass, loss of bone density, and any combinations of these conditions.

The term "periodontal diseases" include all diseases of the periodontal tissues that surround and support the teeth (see, for example, D. M. Williams et al., "*Pathology of Periodontal Disease*", 1992, Oxford University Press). These include the gingiva, cementum, periodontal ligament, alveolar process bone, and dental supporting bone. Specifically, periodontal diseases include gingivitis and periodontitis. Gingivitis is a disease in which inflammation is localized within the gingiva and no lesion occurs in the bone between the teeth and gingiva. Periodontitis is a disease in which gingival inflammation reaches the periodontal ligament and alveolar bone. Left untreated, periodontitis can lead to tooth loss.

The terms "local" and "topical", when herein used to characterize the delivery, administration or application of a compound or composition, is meant to specify that the compound or composition is delivered, administered or applied directly to the site of interest (e.g., in the oral cavity for an oral disorder such as a periodontal disease) for a localized effect. In certain embodiments, local or topical administration is effected without any significant absorption of components of the composition into the subject's blood stream.

As used herein, the term "effective amount" refers to any amount of a molecule, agent, factor or composition that is sufficient to fulfill its intended purpose(s) (e.g., the purpose may be to treat or prevent bone loss, for example, bone loss associated with periodontal disease).

The term "treatment" is used herein to characterize a process/method that is aimed at (1) delaying or preventing the onset of a disease state or condition; (2) slowing down or stopping the progression, aggravation or deterioration of the symptoms of a clinical condition, (3) bringing about ameliorations of the symptoms of the condition; and/or (4) curing the condition. The treatment may be administered before the onset of the condition for a prophylactic action or it may be administered after initiation of the condition for a therapeutic action.

As used herein, the term "physiologically acceptable salts or prodrugs" refers to salts or prodrugs that are, within the scope of sound medical judgment, suitable for use in contact with the tissues of patients without undue toxicity, irritation, allergic response, and the like, commensurate with a reasonable benefit/risk ratio, and effective for their intended use.

The term "salts" refers to any acid addition or base addition salt that retains the biological activity and properties of the corresponding free base or free acid, respectively, and that is not biologically or otherwise undesirable. Acid addition salts are formed with inorganic acids (e.g., hydrochloric, hydrobromic, sulfuric, nitric, phosphoric acids, and the like); and organic acids (e.g., acetic, propionic, pyruvic, maleic, malonic, succinic, fumaric, tartaric, citric, benzoic, mandelic, methanesulfonic, ethanesulfonic, p-toluenesulfonic, salicylic acids, and the life). Base addition salts can be formed with inorganic bases (e.g., sodium, potassium, lithium, ammonium, calcium, magnesium, zinc, aluminum salts, and the like) and organic bases (e.g., salts of primary, secondary, and tertiary amines, substituted amines including naturally-occurring substituted amines, cyclic amines and basic ion exchange resins, such as isopropylamine, trimethylamine, diethylamine, triethylamine, tripropylamine, ethanolamine, 2-dimethyl-aminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like).

The term "prodrug" refers to a compound that, upon in vivo administration, is metabolized or otherwise converted to the biologically, pharmaceutically or therapeutically active form of the compound. The prodrug may be designed to alter the metabolic stability or the transport characteristics of a compound, to mask side effects or toxicity, to improve the flavor of a compound and/or to alter other characteristics or properties of a compound. By virtue of knowledge of pharmacodynamic processes and drug metabolisms in vivo, once a pharmaceutically active compound is identified, those of skill in the pharmaceutical art generally can design prodrugs of the compound (Nogrady, "*Medicinal Chemistry A Biochemical Approach*", 1985, Oxford University Press: N.Y., pages 388-392). Procedures for the selection and preparation of suitable prodrugs are also known in the art. In the context of the present invention, a prodrug is preferably a compound that, upon in vivo administration, is metabolized or otherwise converted to a resolvin.

As used herein, the term "pharmaceutically acceptable carrier or excipient" refers to a carrier medium or an excipient which does not interfere with the effectiveness of the biological activity of the active ingredients and which is not excessively toxic to the host at the concentrations at which it is administered. The term includes solvents, dispersion media, coatings, antibacterial and antifungal agents, isotonic agents, absorption delaying agents, and the like. The use of such media and agents for pharmaceutically active substances is well known in the art (see, for example, "*Remington's Pharmaceutical Sciences*", E. W. Martin, 18$^{th}$ Ed., 1990, Mack Publishing Co.: Easton, Pa., which is incorporated herein by reference in its entirety).

As used herein, the term "osteoconductive" refers to the ability of a compound, composition, process or material to induce the production of osteoblasts from precursor cells, in particular mesenchymal stem cells. The osteoinductive compound, composition, process or material may act directly (e.g., such as a growth factor which interacts with precursor cells to induce the osteoblast differentiation) or it may act indirectly by inducing the production of osteoinductive growth factors.

As used herein, the term "osteoconductive" refers to the ability of a compound, composition, process or material to provide an environment for ingrowth and orientation of osteogenic cells from surrounding tissues.

As used herein, the term "osteogenic" refers to the ability of a compound, composition, process or material to cause (e.g., initiate, promote, facilitate, accelerate, enhance, stimulate, and the like) bone formation.

DETAILED DESCRIPTION OF CERTAIN PREFERRED EMBODIMENTS

As mentioned above, the present invention provides methods and compositions for preventing bone loss and/or enhancing bone growth in a vertebrate subject (human or animal). The inventive methods generally comprise administration of at least one resolvin. The methods of the present invention, which are non-surgical, non-invasive and safe, can be used for the treatment and/or prevention of disease states or conditions associated with bone degradation, bone deterioration or bone degeneration including, but not limited to, periodontal disease, osteoarthritis, metastatic bone disease, and osteolytic bone disease.

I—Resolvins

The methods of the present invention include administration of at least one resolvin. As used herein the term "resolvin" encompasses resolving, resolvin derivatives and analogs, as well as physiologically acceptable salts and prodrugs thereof. In certain embodiments, a single resolvin is administered to the subject. In other embodiments, two or more resolvins are administered to the subject. In such embodiments, administration of the resolvins may be simultaneous (i.e., administration at essentially the same time, e.g., in the form of a mixture of resolvins) or sequential (i.e., administration of the different resolvins at different times).

Resolvins are compounds generated from the interactions between a dietary omega-3-polyunsaturated fatty acid (PUFA) such as eicosapentaenoic acid (EPA) or docosahexaenoic acid (DHA), cyclooxygenase-II (COX-2) and an analgesic, such as aspirin ASA. It was recently demonstrated that ASA treatment of murine in vivo and human tissues in vitro carrying COX-2 initiates the production of novel 17R-hydroxy series docosanoids via previously undescribed pro-inflammatory responses (i.e., cytokine production, peritonitis). During stress, these cellular pathways utilize omega-3 fatty acids to biosynthesize endogenous compounds that serve in anti-inflammation signaling. These new di- and tri-hydroxy -containing compounds derived from omega-3 fatty acids were termed "resolvins", because they (a) are formed within the resolution phase of acute inflammatory response, at least in part, as cell-cell interactions products, (b) "stop" neutrophil entry to sites of inflammation, and (c) reduce exudates (C. N. Serhan et al., J. Exp. Med., 2002, 196: 1025-1037).

Compounds derived from eicosapentaenoic acid are designated as belonging to the E series, given their EPA precursor, and denoted as Resolvins of the E series (e.g., Resolvin E1 or RvE1). Compounds derived from docosahexaenoic acid are denoted as Resolvins of the D series (e.g., Resolvin D1 or RvD1).

Resolvins suitable for use in the methods of the present invention can be any member of the family of compounds known as resolvins, for example, as described in U.S. Pat. No. 6,949,664; U.S. Pat. Appln. Nos. 2005-0238589, 2005-0228047, 2005-0075398, 2004-0116408; and 2003-0191184; PCT application Nos. WO 2005/089744, WO 2005/013908, WO 2004/014835, WO 2003/084305, and WO 2003/053423; and European Pat. Appln. No. EP 1 537 067 (each of which is incorporated herein by reference in its entirety). Other suitable resolvins include those described, for example, in C. N. Serhan et al., J. Exp. Med., 2002, 196: 1025-1037; S. Hong et al., J. Biol. Chem., 2003, 278: 14677-14687; V. L. Marcheselli et al., J. Biol. Chem., 2003, 278: 43807-43817; C. N. Serhan and N. Chiang, Rheum. Dis. Clin. North Am., 2004, 30: 69-95; C. N. Serhan et al., Prostaglandins Other Lipid Mediat., 2004, 73: 155-172; C. N. Serhan et al., Histochem. Cell Biol., 2004, 122: 305-321; C. N. Serhan et al., Lipid, 2004, 39: 1125-1132; C. N. Serhan, Pharmacol. Ther., 2005, 105: 7-21; C. N. Serhan, Curr. Opin. Clin. Nutr. Metab. Care, 2005, 8: 115-121; G. L. Bannenberg et al., J. Immunol., 2005, 174: 4345-4355; U. N. Das, Med. Sci. Monit., 2005, 11: RA233-237; and U. N. Das, J. Assoc. Physicians India, 2005, 53: 623-527; each of which is incorporated herein by reference in its entirety).

In certain embodiments, Resolvin E1 is used for enhancing or promoting bone growth and/or preventing or reducing bone loss. Resolvin E1 belongs to an array of natural bioactive lipids that are generated in vivo from omega-3 polyunsaturated fatty acids by aspirin modified COX-2 (C. N. Serhan et al, J. Exp. Med., 2000, 192: 1197; C. N. Serhan et al., J. Exp. Med., 2002, 196: 1025). The Examples section below describes experiments in which Resolvin E1 is used.

Resolvins used in the methods and compositions of the present invention may be prepared in vivo or in vitro and then substantially purified and isolated by techniques known in the art (see, for example, U.S. Pat. No. 6,670,396, which is incorporated herein by reference in its entirety). Without limitation, the purity of the compounds is generally at least about 90%, preferably at least about 95%, and most preferably at least about 99%. Certain Resolvins used in the inventive methods may be prepared by chemically modifying one or more purified compounds. For example, a purified compound may be chemically modified into a pharmaceutically acceptable salt or prodrug. Additionally or alternatively, one or more hydroxy, thiol or amino groups of the molecule may be protected using methods well known in the art. Resolvins can also be manufactured independently using conventional synthetic methods.

II—Methods of Enhancing Bone Growth and/or Preventing Bone Loss

Methods of the present invention may be used to prevent, inhibit, or reduce bone loss/resorption. Alternatively or additionally, methods of the present invention may be used to increase, enhance, improve or promote bone growth. For example, certain inventive methods may be used to treat, prevent or delay bone degradation, bone degeneration, and/or bone deterioration; to increase or maintain/stabilize bone mass and/or bone density; and/or to reverse bone loss, bone degradation, bone degeneration and/or bone deterioration.

In the methods of the present invention, resolvins may be administered prior to the onset of a pathophysiological condition associated with bone loss for a prophylactic action, or they may be administered after initiation of the condition for a therapeutic action.

Generally, the vertebrate subject (human or other mammal) that can be treated using methods of the present invention suffer from a disease or condition associated with bone loss or are susceptible to a disease or condition associated with bone loss (e.g. exhibit a high or higher risk of developing such a disease or condition, or have been diagnosed with a disease state or condition that is known to cause, to result in or to be associated with bone loss).

Disease states and conditions associated with bone loss that may be treated and/or prevented using the inventive methods include any condition that is characterized by, is accompanied with, is associated with, results in, or induces bone degradation, bone deterioration or bone degeneration, for example leading to loss in bone mass and/or loss in bone density. Examples of such conditions include, but are not limited to, periodontal disease such as periodontitis; bone fracture or deficiency; osteoarthritis; metastatic bone disease; and osteolytic bone disease. Other examples of such conditions include, without limitation, cancers and tumors (such as osteosarcoma and multiple myeloma), renal disease (including acute renal failure, chronic renal failure, renal bone dystrophy and renal reperfusion injury), kidney disease, and premature ovarian failure. Thus, the methods of the present invention may be used for preventing bone loss, for filling in bone defects, stimulating rapid fusion of bone fractures, grafts, and bone-prostheses, and promoting strengthening of osteoporotic bones.

In certain methods of the present invention, resolvins are administered in combination with at least one therapeutic agent that inhibits bone resorption or that promotes bone growth. For example, such an agent can be a bone morphogenetic factor, an anti-resorptive agent, an osteogenic factor, a cartilage-derived morphogenetic protein, a growth hormone, an estrogen, a biphosphonate, a statin, a differentiation factor, or combinations thereof.

In some methods of the present invention, resolvins are administered in combination with one or more additional therapeutic agents. Examples of additional therapeutic agents include, but are limited to, analgesics, anesthetics, antimicrobial agents, antibacterial agents, antiviral agents, antifungal agents, antibiotics, anti-inflammatory agents, antioxidants, antiseptic agents, immunostimulating agents, and combinations thereof. For example, such agents can be antimicrobial compounds and/or non-steroidal anti-inflammatory agents (NSAIDs). In certain embodiments, the additional therapeutic agent or agents are COX-2 inhibitors, such as selective COX-2 inhibitors, e.g., celecoxib, rofecoxib, and/or valdecoxib. In such embodiments, the resolvin and other agents can be administered sequentially or concomitantly/simultaneously.

Alternatively or additionally, resolvins may be administered in combination with (i.e., prior to, concomitant with, and/or following) a medical procedure. For example, the medical procedure may be a surgical intervention to eliminate a periodontal pocket and/or to recontour the bone, or a selective reshaping of tooth surfaces in a subject suffering from a periodontal disease. Alternatively, the medical procedure may be bone grafting, surgical tumor removal, and the like.

III—Resolvin Compositions

In another aspect, the present invention provides pharmaceutical compositions comprising at least one resolvin, at least one therapeutic agent, and at least one pharmaceutically acceptable carrier or excipient. In certain embodiments, the therapeutic agent is selected for its ability to limit bone loss and/or its ability to promote or enhance bone growth. Alternatively or additionally, the therapeutic agent is selected for its ability to increase, stimulate, exacerbate, facilitate or accelerate the action of the resolvin. Alternatively or additionally, the presence of the therapeutic agent imparts to the composition at least one additional therapeutic property/activity (e.g., anti-inflammatory, antibiotic and/or analgesic activity). In certain embodiments, such additional therapeutic activity is beneficial to bone health and/or to health of tissues surrounding bone.

Examples of therapeutic agents that can be used in the compositions of the present invention include, but are not limited to, bone morphogenetic factors, anti-resorptive agents, osteogenic factors, cartilage-derived morphogenetic proteins, growth hormones, estrogens, biphosphonates, statins, differentiation factors, and combinations thereof. Other examples of therapeutic agents suitable for use in the inventive compositions, but are not limited to, analgesics, anesthetics, antimicrobial agents, antibacterial agents, antiviral agents, antifungal agents, antibiotics, anti-inflammatory agents, antioxidants, antiseptic agents, immunostimulating agents, and combinations thereof.

As will be appreciated by one of ordinary skill in the art, a therapeutic agent may be a synthetic or naturally-occurring compound; a single molecule, a complex of different molecules or a mixture/composition of different molecules.

Therapeutic Agents for Bone Growth Stimulation or Bone Loss Prevention

In certain embodiments, pharmaceutical compositions of the present invention comprise a therapeutic agent that promotes bone growth or inhibits bone resorption. As used herein, the term "therapeutic agent that promotes bone growth or inhibits bone resorption" refers to any compound, agent, factor or composition that directly or indirectly has a beneficial/therapeutic effect on a bone or bone tissue undergoing degradation, degeneration, deterioration, loss of bone mass and/or loss of bone density. In certain embodiments, the therapeutic agent promotes (i.e., initiate, facilitate, accelerate, enhance, increase, stimulate, and the like) bone formation/growth. In other embodiments, the therapeutic agent inhibits (i.e., prevents, reduces, minimizes, limits, delays, maintains, stabilizes, and the like) bone loss/resorption. In still other embodiments, the therapeutic agent promotes bone formation and inhibits bone resorption.

For example, the therapeutic agent may be a biomolecule that is naturally present within the body and/or that is naturally secreted at a site undergoing bone growth/formation and plays a role in one or more steps of the bone formation process. As will be apparent to those of ordinary skill in the art, variants, synthetic analogs, derivatives, and active portions of these biomolecules can, alternatively, be used in the inventive compositions as long as they exhibit substantially the same type of property/activity as the native biomolecule. Such variants, synthetic analogs, derivatives or active portions are intended to be within the scope of the term "therapeutic biomolecule".

Therapeutic biomolecules may be extracted from mammalian tissues and used in the present invention either crude or after purification. Alternatively, they may be prepared chemically or by conventional genetic engineering techniques, such as via expression of synthetic genes or of genes altered by site-specific mutagenesis.

Therapeutic agents that increase bone mass or bone density include, but are not limited to, growth factors (such as IGF-1, IGF-2, macrophage growth factor, platelet derived growth factors (PFGDs), fibroblast growth factors (FGFs), epidermal growth factors (EGFs), transforming growth factors (TGFs), cartilage-derived morphogenic protein (CDMP-1, CDMP-2, CDMP-3) and connective tissue activating peptides (CTAPs), minerals (such as calcium, aluminum, strontium and fluoride), vitamins (such as Vitamin D3), hormones (such as parathyroid hormone (PTH), and parathyroid hormone related protein (PTHrP)); prostaglandins (such as PDG1, PDG2, PGE2, PGE1 and PGF2); inhibitors of 15-lipoxygenase; dexamethasone; statins; and bone morphogenic proteins (such as BMP-2, BMP-4 and BMP-7).

In certain embodiments, the therapeutic agent is a transforming growth factor beta (TGF-β). TGF-βs are extracellular polypeptides that are implicated in a broad range of biological processes (J. Massagué, Annu. Rev. Cell. Biol., 1990, 6: 597-641) and play a central role in key events during embryogenesis, adult tissue repair, and immunosuppression (M. B. Sporn and A. B. Roberts, J. Cell. Biol., 1992, 119: 1017-1021; S. W. Wahl, J. Clin. Immunol., 1992, 12: 61-74; D. M. Kingsley, Genes Dev., 1994, 8: 133-146). TGF-β is known to evoke proliferation and differentiation of osteoblasts (M. Centrella et al., J. Bone Join. Surg., 1991, 73: 1418-1428; T. A. Mustoe et al., Science, 1987, 237: 1333-1336; L. S. Beck et al., J. Bone Miner. Res., 1991, 6: 961-968). TGF-β is also known to play an important role in the early phase of osteogenesis (S. Dieudonne et al., J. Cell. Biochem., 1999, 76: 231-243). TGF-β to be used in the inventive compositions may be produced from recombinant cell cultures. Alternatively, TGF-β may be derived from blood platelets or any other mammalian tissue using any suitable method. Preferably, TGF-β is derived from human tissue. However, since TGF-β is not species specific, it may, alternatively, be derived from animal sources such as bone or porcine sources. In certain cases, TGF-β is preferably purified to essential homogeneity using, for example, sequential gel filtration, cation-exchange chromatography, or high performance liquid chromatography.

In other embodiments, the therapeutic agent is a bone morphogenic protein (BMP). BMP is a bone-forming protein that has been reported to stimulate pluripotential cells to be differentiated into chondrocytes and osteogenesis cells, and to play an important role in bone regeneration (M. R. Urist, Science, 1965, 150: 893-899; M. R. Urist and B. S. Strates, J. Dent. Res., 1971, 50: 1392-1406; J. M. Wozney, Mol. Reprod. Dev., 1992, 32: 160-167; J. M. Wozney et al., Science, 1988, 242: 1528-1534; I. Ono et al., Craniofac. Surg., 1996, 7: 418-425). BMPs that may be used in the present invention include, but are not limited to, BMP-1, BMP-2α, BMP-2β, BMP-3β, MP-4, BMP-5, BMP-6, BMP-7, BMP-8β, BMP-9, BMP-10, BMP-11, BMP-12, BMP-13, BMP-14, and BMP-15.

In still other embodiments, the composition comprises sources of calcium and phosphate to locally enhance the soluble concentration of dissolved calcium ($Ca^{2+}$) and phosphate ($PO_4^-$) within and around the site of application of the composition. The calcium source and the phosphate source may be the same material or may be different materials. Suitable sources of calcium for use in the present invention include any acidic calcium salt, such as calcium phosphate salts (e.g., monocalcium phosphate, calcium phosphate dihydrate (also known as dical), and calcium pyrophosphate) or calcium citrate salts. Suitable sources of phosphate for use in the present invention include any phosphate salt, such as calcium phosphate salts (e.g., acidic calcium phosphate salts) and sodium phosphate salts. Examples of acidic calcium phosphate salts include hydrogen phosphate dihydrate, monocalcium phosphate, and calcium pyrophosphate.

In yet other embodiments, the therapeutic agent is a statin. The terms "statins" and "HMG-CoA reductase inhibitors" are used herein interchangeably and refer to compounds that inhibit the enzyme 3-hydroxy-3-methylglutaryl coenzyme A (HMG-CoA) reductase. HMG-CoA reductase is the principal rate-limiting enzyme involved in cellular cholesterol biosynthesis. Statins enhance the production of osteoblasts, the cells that produce new bone, and enhance osteoblast differentiation (E. Harris et al., Mol. Cell. Diff., 1995, 3: 137-147; G. Mundy et al., Science, 1999, 286: 1946-1949). In particular, statins have been shown to promote BMP production systematically or in fracture sites (U.S. Pat. Nos. 6,022,887; 6,080,779; and 6,376,476). Examples of statins suitable for use in the present invention include, but are not limited to, lovastatin, pravastatin, velostatin, simvastatin, fluvastatin, cerivastatin, mevastatin, dalvastatin, fluindostatin, atorvastatin, a prodrug thereof, or a physiologically acceptable salt thereof.

Agents that prevent bone loss/resorption that can be used in the present invention include, but are not limited to, progestins, estrogen, estrogen/progestin combinations, estrone, estriol, 17α- or 17β-ethynyl estradiol, SB242784, polyphosphonates, and bisphosphonates. Commercially available bisphosphonates include, etidronate, clodronate, tiludronate, alendronate, pamidronate, and ibandronate.

Pain Relieving Agents

The present invention provides compositions that can be used to prevent or alleviate pain, soreness or discomfort while preventing bone loss and/or promoting bone formation. Pain relieving agents for use in the present invention include, but are not limited to, compounds, molecules or drugs which have a temporary analgesic, anesthetic, numbing, relaxing, and/or calming effect. In certain embodiments, these compounds, molecules or drugs have a pain-relieving effect when applied topically.

Analgesics suitable for use in the present invention include non-steroidal, anti-inflammatory drugs (NSAIDs). NSAIDs have analgesic, antipyretic and anti-inflammatory activity.

They act peripherally to provide their analgesic effect by interfering with the synthesis of prostaglandin, through cyclooxygenase (COX) inhibition. There are many different types of NSAIDs, including aspirin and other salicylates. Examples include, but are not limited to, ibuprofen, naproxen, sulindac, diclofenac, piroxicam, ketoprofen, diflunisal, nabumetone, etodolac, oxaprozin, and indomethacin. Several of the more potent NSAIDs have been developed into topical products for local applications to painful areas of the body.

Anesthetics, such as xylocaine, lidocaine or benzocaine (or other drugs such as those described below) may be added to an analgesic compositions of the present invention to provide an immediate but short-term pain relief until the analgesic agent becomes fully effective. Anesthetics that are suitable for use in the practice of the present invention include sodium-channel blockers. Sodium-channel blockers prevent the generation and conduction of nerve impulses by decreasing or preventing the large transient increase in the permeability of excitable membranes to sodium ions, $Na^+$.

Examples of sodium-channel blockers include, but are not limited to, ambucaine, amolanone, amylcaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, etidocaine, euprocin, fenalcomine, formocaine, hexylcaine, hydroxyteteracaine, isobutyl p-aminobenzoate, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and active derivatives, prodrugs, analogs, pharmaceutically acceptable salts, or mixtures thereof.

Anti-Infective Agents

Anti-infective agents for use in the compositions of the present invention are compounds, molecules or drugs, which have an anti-infective activity (i.e., they can decrease the risk of infection, prevent infection, or inhibit, suppress, combat or otherwise treat infection). In certain embodiments, these compounds, molecules or drugs have an anti-infective activity when applied topically. Anti-infective agents suitable for use in the present invention include, but are not limited to, antiseptics, antimicrobial agents, antibiotics, antibacterial agents, antiviral agents, antifungal agents, antiprotozoan agents, immuno-stimulating agents, and any combinations thereof.

Antiviral agents may be present in compositions to prevent viral infection and/or to reduce viral titers at a site. Suitable antiviral agents include RNA synthesis inhibitors, protein synthesis inhibitors, immunostimulating agents, and protease inhibitors. Antiviral agents may, for example, be selected from the group consisting of acyclovir, amantadine hydrochloride, foscarnet sodium, ganeiclovir sodium, phenol, ribavirin, vidarabine, and zidovudine.

Antifungal agents may be selected from a wide variety of therapeutic agents. For example, lactic acid (i.e., 2-hydroxypropanoic acid) is an antifungal agent that is known to inhibit the growth of pathogens. Sorbic acid (i.e., 2,4-hexadienoic acid) is a natural antifungal agent that kills *Candida albicans*. Other antifungal agents include, but are not limited to, Amphotericin B, Ciclopirox, Clotrimazole, Enilconazole, Econazole, Fluconazole, Griseofulvin, Halogropin, Introconazole, Ketoconazole, Miconazole, Naftifine, Nystatin, Oxiconazole, Sulconazole, Thiabendazole, Terbinafine, Tolnaftate, Undecylenic acid, Mafenide, Silver Sulfadiazine, and Carbol-Fushsin.

Antibiotics and other antimicrobial agents may be selected from the group consisting of bacitracin; the cephalosporins (such as cefadroxil, cefazolin, cephalexin, cephalothin, cephapirin, cephradine, cefaclor, cefamandole, cefonicid, ceforanide, cefoxitin, cefuroxime, cefoperazone, cefotaxime, cefotetan, ceftazidime, ceftizoxime, ceftriaxone, and meropenem); cycloserine; fosfomycin, the penicillins (such as amdinocillin, ampicillin, amoxicillin, azlocillin, bacamipicillin, benzathine penicillin G, carbenicillin, cloxacillin, cyclacillin, dicloxacillin, methicillin, mezlocillin, nafcillin, oxacillin, penicillin G, penicillin V, piperacillin, and ticarcillin); ristocetin; vancomycin; colistin; novobiocin; the polymyxins (such as colistin, colistimathate, and polymyxin B); the aminoglycosides (such as amikacin, gentamicin, kanamycin, neomycin, netilmicin, paromomycin, spectinomycin, streptomycin, and tobramycin), the tetracyclines (such as demeclocycline, doxycycline, methacycline, minocycline, and oxytetracycline); carbapenems (such as imipenem); monobactams (such as aztreonam); chloramphenicol; clindamycin; cycloheximide; fucidin; lincomycin; puromycin; rifampicin, other streptomycins; the macrolides (such as erythromycin and oleandomycin); the fluoroquinolones; actinomycin; ethambutol; 5-fluorocytosine; griseofulvin; rifamycins; the sulfonamides (such as sulfacytine, sulfadiazine, sulfisoxazole, sulfamethoxazole, sulfamethizole, and sulfapyridine); and trimethoprim.

Other suitable antibacterial agents include, but are not limited to, bismuth containing compounds (such as bismuth aluminate, bismuth subcitrate, bismuth subgalate, and bismuth subsalicylate); nitrofurans (such as nitrofurazone, nitrofurantoin, and furozolidone); metronidazole; tinidazole; nimorazole; and benzoic acid.

Antiseptic agents may be selected from the group consisting of benzalkonium chloride, chlorhexidine, benzoyl peroxide, hydrogen peroxide, hexachlorophene, phenol, resorcinol, and cetylpyridinium chloride.

Immunostimulating agents suitable for use in the inventive compositions may be selected from a wide range of therapeutic agents, such as interleukin 1 agonists, interleukin 2 agonists, interferon agonists, RNA synthesis inhibitors, and T cell stimulating agents.

Anti-Inflammatory Agents

The present invention provides anti-inflammatory compositions that can be used to reduce the duration and/or severity of inflammation, while preventing bone loss and/or promoting bone formation. Anti-inflammatory agents for use in the present invention are compounds, molecules or drugs which have an anti-inflammatory activity (i.e., they can prevent or reduce the duration and/or severity of inflammation; prevent or reduce injury to tissue; and/or provide relief from at least one of the manifestations of inflammation such as erythema, swelling, tissue ischemia, fever, and the like). In certain embodiments, these compounds, molecules or drugs have an anti-inflammatory activity when applied topically.

Anti-inflammatory agents suitable for use in the present invention may be selected from a wide variety of steroidal and non-steroidal anti-inflammatory agents. Examples of NSAIDs can be found above. Examples of steroidal anti-inflammatory agents include, but are not limited to, aclomethasone dipropionate, flunisolide, fluticasone, budesonide, triamcinolone, triamcinoline acetonide, beclomethasone dipropionate, betamethasone valerate, betamethasone dipropionate, hydrocortisone, cortisone, dexamethason, mometasone furoate, prednisone, methylprednisolone aceponate, and prednisolone.

Anti-inflammatory agents may, alternatively or additionally, be selected from the wide variety of compounds, molecules, and drugs exhibiting antioxidant activity. Antioxidants are agents that can prevent or reduce oxidative damage to tissue. Antioxidants may be selected from the group consisting of vitamin A (retinal), vitamin B (3,4-didehydroretinol), vitamin C (D-ascorbic acid, L-ascorbic acid), α-carotene, β-carotene, γ-carotene, δ-carotene, vitamin E (α-tocopherol), β-tocopherol, γ-tocopherol, δ-tocopherol, tocoquinone, tocotrienol, butylated hydroxy anisole, cysteine, and active derivatives, analogs, precursors, prodrugs, pharmaceutically acceptable salts or mixtures thereof.

The amount of therapeutic agent(s) (e.g., osteogenic factors, growth hormones, analgesic, anti-inflammatory agent) present in a composition of the invention may vary depending upon the dosage recommended or permitted for the particular therapeutic agent, as well as the type of bone loss being treated and the presence and nature of other ingredients/components in the composition. In certain embodiments, the amount of therapeutic agent present is the ordinary dosage required to obtain the desired result through topical administration. Such dosages are either known to or readily determined by the skilled practitioner in the pharmaceutical or medical arts.

IV—Formulation, Dosage and Administration of Resolvins

Resolvins may be administered per se or as a pharmaceutical composition, admixed with a pharmaceutically acceptable carrier or excipient. Resolvins, or pharmaceutical compositions thereof, can be administered to a subject using any suitable means. In general, suitable means of administration include, but are not limited to, topical, oral, parenteral (e.g., intravenous, subcutaneous or intramuscular), rectal, intracisternal, intravaginal, intraperitoneal, ocular or nasal routes. In certain preferred embodiments, resolvins or compositions thereof are administered topically.

Depending on the mode of administration, resolvins or compositions thereof may be in the form of liquid, solid, or semi-solid dosage preparations. For example, the compositions may be formulated as solutions, dispersions, suspensions, emulsions, mixtures, lotions, liniments, jellies, ointments, creams, pastes, gels, hydrogels, aerosols, sprays, microcapsules, microspheres, nanoparticles, pellets, agarose or chitosan beads, capsules, granules, granulates, powders, plasters, bandages, sheets, foams, films, sponges, dressings, drenches, bioadsorbable patches, sticks, delivery devices and implants.

For topical administration to the oral cavity, resolvins or compositions thereof may be formulated as solutions, suspensions, dispersions, ointments, creams, pastes including toothpastes, gels, powders including tooth powders, toothpastes, lozenges, salve, chewing gum, aerosols, sprays including mouth sprays, pastilles, sachets, mouthwashes, toothpicks, tablets, capsules, and dental floss. Such formulations may include topical, oral carriers such as anti-caries agents, anti-plaque agents, anti-calculus agents, anti-inflammatory agents, dental abrasives, surfactants, flavoring agents, sweetening agents, binders, humectants, thickening agents, buffering agents, preservatives, coloring agents, and pigments, flavorants, filers, stabilizers, ethanol and water.
Formulation Resolvins and pharmaceutical compositions thereof may be formulated according to general pharmaceutical practice (see, for example, "*Remington's Pharmaceutial Sciences*" and "*Encyclopedia of Pharmaceutical Technology*", J. Swarbrick, and J. C. Boylan (Eds.), Marcel Dekker, Inc: New York, 1988).

Pharmaceutically acceptable carriers, vehicles, and/or excipients for use in the practice of the present invention can be routinely selected for a particular use by those skilled in the art. These include, but are not limited to, solvents, buffering agents, inert diluents or fillers, suspending agents, dispersing or wetting agents, preservatives, stabilizers, chelating agents, emulsifying agents, anti-foaming agents, gel-forming agents, ointment bases, penetration enhancers, humectants, and emollients.

Examples of solvents are water, alcohols, vegetable, marine and mineral oils, polyethylene glycols, propylene glycols, glycerol, and liquid polyalkylsiloxanes. Inert diluents or fillers may be sucrose, sorbitol, sugar, mannitol, microcrystalline cellulose, starches, calcium carbonate, sodium chloride, lactose, calcium phosphate, calcium sulfate, or sodium phosphate. Examples of buffering agents include citric acid, acetic acid, lactic acid, hydrogenophosphoric acid, and diethylamine. Suitable suspending agents are, for example, naturally occurring gums (e.g., acacia, arabic, xanthan, and tragacanth gum), celluloses (e.g., carboxymethyl-, hydroxyethyl-, hydroxypropyl-, and hydroxypropylmethyl-cellulose), alginates and chitosans. Examples of dispersing or wetting agents are naturally occurring phosphatides (e.g., lecithin or soybean lecithin), condensation products of ethylene oxide with fatty acids or with long chain aliphatic alcohols (e.g., polyoxyethylene stearate, polyoxyethylene sorbitol monooleate, and polyoxyethylene sorbitan monooleate).

Preservatives may be added to a resolvin or pharmaceutical composition thereof to prevent microbial contamination that can affect the stability of the formulation and cause infection in the patient. Suitable examples of preservatives include parabens (such as methyl, ethyl, propyl, p-hydroxybenzoate, butyl, isobutyl, and isopropylparaben), potassium sorbate, sorbic acid, benzoic acid, methyl benzoate, phenoxyethanol, bronopol, bronidox, MDM hydantoin, iodopropynyl butylcarbamate, benzalconium chloride, cetrimide, and benzylalcohol. Examples of chelating agents include sodium EDTA and citric acid.

Examples of emulsifying agents are naturally occurring gums, naturally occurring phosphatides (e.g., soybean lecithin; sorbitan mono-oleate derivatives), sorbitan esters, monoglycerides, fatty alcohols, and fatty acid esters (e.g., triglycerides of fatty acids). Anti-foaming agents usually facilitate manufacture, they dissipate foam by destabilizing the air-liquid interface and allow liquid to drain away from air pockets. Examples of anti-foaming agents include simethicone, dimethicone, ethanol, and ether.

Examples of gel bases or viscosity-increasing agents are liquid paraffin, polyethylene, fatty oils, colloidal silica or aluminum, glycerol, propylene glycol, carboxyvinyl polymers, magnesium-aluminum silicates, hydrophilic polymers (such as, for example, starch or cellulose derivatives), water-swellable hydrocolloids, carragenans, hyaluronates, and alginates. Ointment bases suitable for use in the practice of the present invention may be hydrophobic or hydrophilic, and include paraffin, lanolin, liquid polyalkylsiloxanes, cetanol, cetyl palmitate, vegetable oils, sorbitan esters of fatty acids, polyethylene glycols, and condensation products between sorbitan esters of fatty acids, ethylene oxide (e.g., polyoxyethylene sorbitan monooleate), and polysorbates.

Examples of humectants are ethanol, isopropanol glycerin, propylene glycol, sorbitol, lactic acid, and urea. Suitable emollients include cholesterol and glycerol. Examples of skin protectants include vitamin E, allatoin, glycerin, zinc oxide, vitamins, and sunscreen agents.

Resolvin pharmaceutical compositions may, alternatively or additionally, comprise other types of excipients including, thickening agents, bioadhesive polymers, and permeation enhancing agents.

Thickening agents are generally used to increase viscosity and improve bioadhesive properties of pharmaceutical compositions. Examples of thickening agents include, but are not limited to, celluloses, polyethylene glycol, polyethylene oxide, naturally occurring gums, gelatin, karaya, pectin, alginic acid, and povidone. Particularly interesting are thickening agents with thixotropic properties (i.e., agents whose viscosity is decreased by shaking or stirring). The presence of such an agent in a composition allows the viscosity of the composition to be reduced at the time of administration to facilitate its local application and, to increase after application so that the composition remains at the site of administration.

Bioadhesive polymers are useful to hydrate skin or mucosa and enhance its permeability. Bioadhesive polymers can also function as thickening agents. Examples of bioadhesive polymers include, but are not limited to, pectin, alginic acid, chitosan, polysorbates, poly(ethyleneglycol), oligosaccharides and polysaccharides, cellulose esters and cellulose ethers, and modified cellulose polymers.

Permeation enhancing agents are vehicles containing specific agents that affect the delivery of active components through the skin/mucosa. Permeation enhancing agents are generally divided into two classes: solvents and surface active compounds (amphiphilic molecules). Examples of solvent permeation enhancing agents include alcohols (e.g., ethyl alcohol, isopropyl alcohol), dimethyl formamide, dimethyl sulfoxide, 1-dodecylazocyloheptan-2-one, N-decyl-methylsulfoxide, lactic acid, N,N-diethyl-m-toluamide, N-methylpyrrolidone, nonane, oleic acid, petrolatum, polyethylene glycol, propylene glycol, salicylic acid, urea, terpenes, and trichloroethanol. The surfactant permeation enhancing agent in the present inventive pharmaceutical compositions may be nonionic, amphoteric, cationic, or zwitterionic. Suitable nonioinic surfactants include poly(oxyethylene)-poly(oxypropylene) block copolymers, commercially known as poloxamers; ethoxylated hydrogenated castor oils; polysorbates, such as Tween 20 or Tween 80. Amphoteric surfactants include quaternized imidazole derivatives, cationic surfactants include cetypyridinium chloride, and zwitterionic surfactants include the betaines and sulfobetaines.

Controlled Release of Resolvins

In certain embodiments, resolvins pharmaceutical compositions are formulated to provide a local controlled release of one or more of the active components. Any pharmaceutically acceptable carrier vehicle or formulation suitable for local administration may be employed. Slow release formulations known in the art include coated-pellets, polymer formulations (such as vesicles or liposomes), microparticles (e.g., microspheres or microcapsules).

A wide variety of biodegradable materials may be used to provide controlled release. The controlled release material should be biocompatible and be degraded, dissolved or absorbed in situ in a safe and pharmaceutically acceptable manner so that the material is removed from the site of administration by natural tissue processes and in a suitable amount of time (e.g., less than one year, less than 6 months, and less than one month, less than one week, less than one day or less than a few hours). The controlled release carrier should not cause any unwanted local tissue reaction, nor should it induce systemic or local toxicity.

Suitable controlled release biodegradable polymers for use in the formulation of the compositions of the invention may comprise polylactides, polyglycolides, poly(lactide-co-glycolides), polyanhydrides, polyorthoesters, polycaprolactones, poly-saccharides, poly-phosphazenes, proteinaceous polymers and their soluble derivatives (such as gelation biodegradable synthetic polypeptides, alkylated collagen, and alkylated elastin), soluble derivatives of polysaccharides, polypeptides, polyesters, and polyorthoesters.

The pharmacokinetic release profile of these formulations may be first order, zero order, bi- or multi-phasic, to provide the desired therapeutic effect over the desired period of time. A desired release profile can be achieved by using a mixture of polymers having different release rates and/or different percents loading of the component(s) of the composition. Methods for the manufacture of coated-pellets, liposomes, microspheres and microcapsules are well known in the art.

Dosage

Administration of resolvins or compositions of the present invention will be in a dosage such that the amount delivered is effective for the intended purpose. The route of administration, formulation and dosage administered will be dependent upon the nature, size, and location of the particular site to be treated, the severity of the bone loss if already present, the presence of any infection, the age, weight and health condition of the patient as well as upon the potency, bioavailability, and in vivo half-life of the composition used. These factors are readily determinable by the attending physician in the course of the therapy. Alternatively or additionally, the dosage to be administered can be determined from studies using animal models for the particular type of site/disease to be treated. The total dose required for each treatment may be administered by multiple doses or in a single dose. Adjusting the dose to achieve maximal efficacy based on these or other methods are well known in the art and are within the capabilities of trained physicians. As studies are conducted, further information will emerge regarding the appropriate dosage levels and duration of treatment for various types of bone loss or degradation.

Administration

The mode of administration of resolvins or resolvin compositions of the invention will mainly depend on the form of the preparation chosen. For example, gels, lotions, creams and ointments may be manually applied or sprayed (either with a manually-activated pump or with the aid of a suitable pharmaceutically acceptable propellant) onto the surface area in need of treatment. Alternatively, a brush, syringe, spatula or a specifically designed container (such as a tube with a narrow tip) can be used to apply the preparation.

In certain embodiments, resolvins or pharmaceutical compositions thereof are used during or after surgery (e.g., intervention to eliminate a periodontal pocket and/or recontour the bone, selective reshaping of tooth surfaces, bone grafting, tumor ablation and the like). Under such circumstances, resolvins or pharmaceutical compositions thereof can be applied to the bone being surgically treated, for example, before closure using sutures, stapes, adhesive strips or tissue adhesives. The composition may, for example, comprise an analgesic and/or anesthetic agent to provide local anesthesia or numbness during closure and/or to prevent or reduce pain during and after the operative procedure. Alternatively or additionally, the composition may comprise an anti-infective agent to prevent infection. When the surgical procedure is related to cancer tumor ablation, the composition may further comprise a chemotherapeutic anti-cancer agent to prevent regrowth of the tumor from any residual cancer cells. When the surgical procedure involves bone grafting, the composition may further comprise an immunosuppressant to prevent graft rejection.

V—Kits

In another aspect, the present invention provides kits comprising at least one resolvin and at least one therapeutic agent that promotes bone growth or inhibits bone resorption. The at least one resolvin and at least one therapeutic agent in the kit may be provided separately or as a mixture.

For example, a kit may comprise two separate containers, with the first container comprising the resolvin or a composition thereof, and the second container comprising the therapeutic agent or a composition thereof. A kit may alternatively comprise two separate containers, with the first container comprising a mixture or composition comprising the resolvin and therapeutic agent, and the second container comprising a suitable medium intended to be added to the first container before use in order to obtain a ready-to-use composition. Alternatively or additionally, a kit may be composed of a container comprising a mixture or composition comprising the resolvin and therapeutic agent and a tool (e.g., brush, syringe, spatula) to be used to apply the mixture or composition of the first composition.

In certain embodiments, the individual containers (e.g., vials, ampoules, flasks, bottles, tubes with a narrow tips) are maintained in close confinement for commercial use.

An inventive kit may further comprise instructions for using the resolvin and therapeutic agent (and any other additional agents and reagents) according to the present invention. Instructions for using the kit according to one or more methods of the invention may comprise information about the indications, preferred mode(s) of administration, preferred regimen(s), preferred dosages, potential side effects, and the like. The kits may also comprise a notice in the form prescribed by a government agency (e.g., FDA) regulating the manufacture, use or sale of pharmaceuticals. An identifier, e.g., a bar code, radio frequency, ID tags, etc., may be present in or on the kit. The identifier can be used, for example, to uniquely identify the kit for purposes of quality control, inventory control, tracking movement between workstations, etc. In certain embodiments of the invention, the kits are manufactured in accordance with good manufacturing practices as required by government agency—(e.g., FDA) approved pharmaceuticals.

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Materials and Methods

Animal Model

Study protocol and experimental design have been reviewed and approved by the Boston University Medical Center Institutional Animal Care and Use Committee (BUMC IACUC) prior to study initiation (IACUC protocol #: AN-13948). In addition, BUMC Institutional Biohazard Committee (IBC) has approved the use of *Porphyromonas gingivalis* (*P. gingivalis*) in this animal model to induce periodontal disease (IBC protocol #: A-269).

New Zealand White rabbits (male, 3.5-4.0 kg each) were used in the experiments presented herein. The animals were distributed as follows: Group A: Ligature+*P. gingivalis* (or "Periodontal Disease, No Treatment" group); Group B: Ligature+*P. gingivalis*+vehicle alone (or "Vehicle" group); Group C: Ligature+*P. gingivalis*+Resolvin E1 in vehicle (or "RvE1" group). All animals were purchased from Pine Acre Farms (Berthoud, Colo.). The weight of the animals was strictly controlled and all animals weighed between 3.5-4.0 kg at the time of the initial experimentation. The animals were kept in individual cages, received water ad libitum, and were fed with specialized food (chow) for at least 5 days for acclimatization by experienced and licensed laboratory technicians at the Laboratory Animal Science Center at BUMC (BUMC LASC).

Experimental Periodontitis

Ligature placement was performed under general anesthesia using ketamine (40 mg/kg) and xylazine (5 mg/kg) injections. Animals had a 3-0 silk suture placed around the second premolar of both mandibular quadrants. *P. gingivalis* (strain A74376) was grown as previously described. Briefly, bacteria were cultured on agar plates containing trypticase soy agar supplemented with 0.5% (w/v) yeast extract, 5% defibrinated sheep red blood cells, 5 µg hemin, and 1 µg/mL vitamin K Plates were incubated for 3 days at 37° C. in jars anaerobically maintained through palladium catalyzed hydrogen/carbon dioxide envelopes (GasPak Plus, BD Microbiology Systems, Sparks, Md.). Colonies were randomly selected and anaerobically cultured overnight at 37° C. in Schaedler's broth supplemented with vitamin K and hemin. Bacteria numbers were spectrophotometrically determined at 600 nm and $10^9$ CFU (0.8 OD) were mixed with carboxymethylcellulose to form a thick slurry, which was applied topically to the ligated teeth. The sutures were checked at every appointment, and lost or loose sutures were replaced.

Topical Application of Resolvin E1

Figure 1:
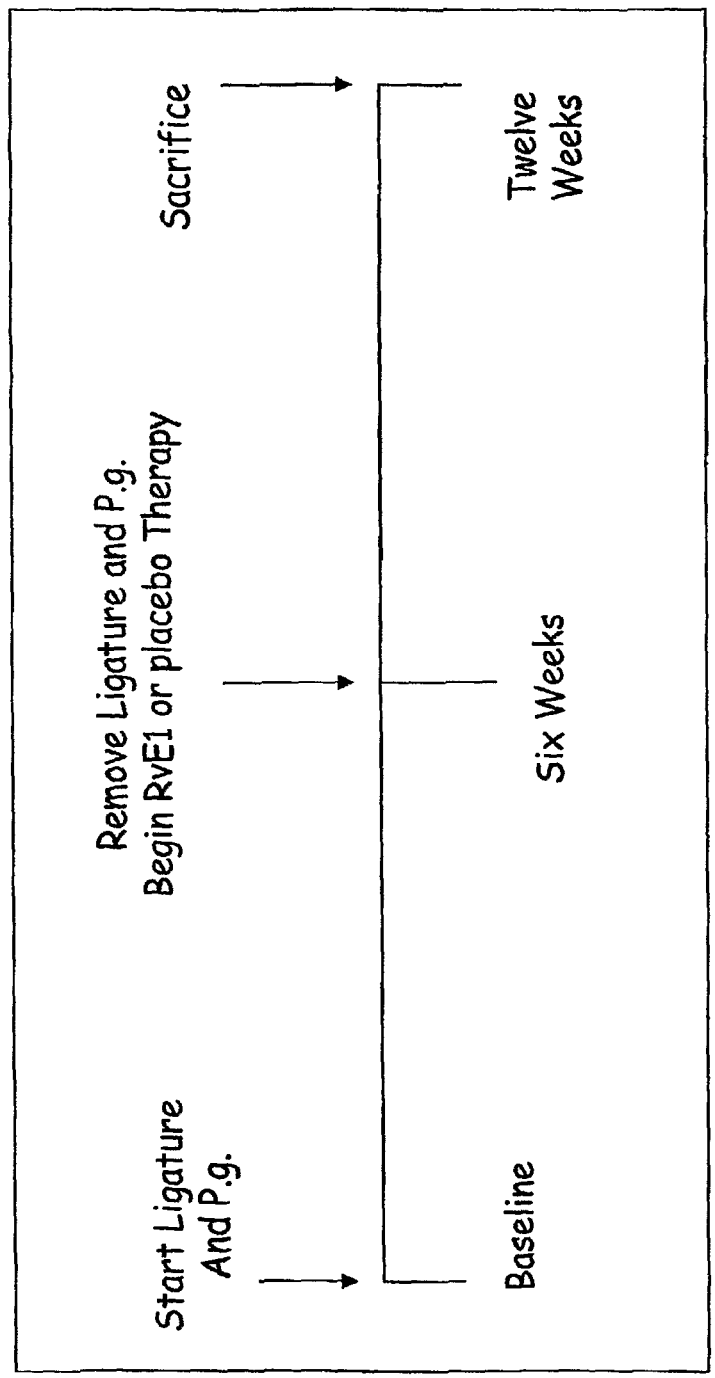
FIG. 1 is a scheme depicting the design of experiments reported in the Examples section.

As shown on FIG. 1, six weeks after ligature and *P. gingivalis*, topical applications were performed every other day for 6 weeks and under the inhalation anesthesia using isoflurane (4.0 MAC/2.0 MAC). In the "Vehicle" group, ethanol (7 µL), which was used as a carrier vehicle for resolvin E1 and in group C, resolvin E1 (7 µg/µL) suspended in ethanol was applied. At the end of the study (i.e., twelve weeks after induction of periodontal disease by ligature and *P. gingivitis*), the animals were euthanized using overdose pentobarbital (euthanasia) injections (120 mg/kg) according to the protocol approved by the IACUC. No adverse events were observed during experimental procedures throughout the study with regard to the animal care and no animals were prematurely lost during the study.

Morphometric Analysis

After sacrificing the animals, the mandible was dissected free of muscles and soft tissue, keeping the attached gingiva intact with the bone. Then the mandible was split into two halves from the midline between the central incisors. One half was taken for morphometric analysis of bone loss and the other half was used for histological evaluation of periodontitis. Half of the sectioned mandible was defleshed by immersing in 10% hydrogen peroxide (10 minutes, room temperature). The soft tissue was removed carefully and then the mandible was stained with methylene blue for good visual distinction between the tooth and the bone (see FIG. 4). Next, the bone level around the second premolar was measured directly by a 0.5 mm calibrated periodontal probe.

Measurements were made at three points each, at buccal and lingual sides, for crestal bone level. A mean crestal bone level around the tooth was calculated. Similarly, for the proximal bone level, measurements were made at mesial and distal aspects of the tooth. The measurements were taken from both the buccal and lingual sides on both proximal aspects of the second premolar and the mean proximal bone level was calculated. The bone level was also quantified by Image Analysis (Image-Pro Plus 4.0, Media Cybernetics, Silver Spring, Md.). The sectioned mandible was mounted and photographed using an inverted microscope at 10×. The captured image was also analyzed as above and the mean crestal bone level around the tooth was calculated in millimeters.

Radiographic Analysis

The percentage of the tooth within the bone was calculated radiographically using Bjorn technique (A. Jain et al., Infect. Immun., 2003, 71: 6012-6018). The radiographs were taken with a digital X-ray (Schick Technologies Inc., Long Island City, N.Y.). To quantify bone loss, the length of the tooth from the cusp tip to the apex of the root was measured, as was the length of the tooth structure outside the bone, measured from the cusp tip to the coronal extent of the proximal bone. From these measurements, the percentage of the tooth within the bone was calculated. Bone values are expressed as the percentage of the tooth in the bone (i.e., [length of tooth in bone×100]/total length of tooth).

Histological Analysis

For histological analysis, the other half of the mandible was immersed in a volume of immunocal (Decal Corporation, Tallman, N.Y.) equal to at least 10 times the size of the section; the solution was replaced every 24 hours for 72 hours.

Decalcification was assessed and confirmed by serial radiographs, which were taken every other day during two weeks. After decalcification, the tissues were rinsed for 1-3 minutes in running water, placed in Cal-Arrest (Decal Corporation, Tallman, N.Y.) in order to neutralize the pH of the tissue, enhance embedding and staining characteristics, and stop further decalcification so that the tissue does not become over-decalcified. The tissue was kept in this solution for 2-3 minutes, rinsed again in flowing deionized water for at least 3 minutes and kept in formalin for at least 24 hours before embedding in paraffin. Thin sections (5 µm) were cut and sections were conventionally stained with hematoxylin and eosin (H&E) to identify the cellular composition of the inflammatory infiltrates, and one hundred seventy 5 µm sections were stained with tartrate-resistant acid phosphatase (TRAP) to detect osteoclastic activity.

RESULTS

Figure 2:
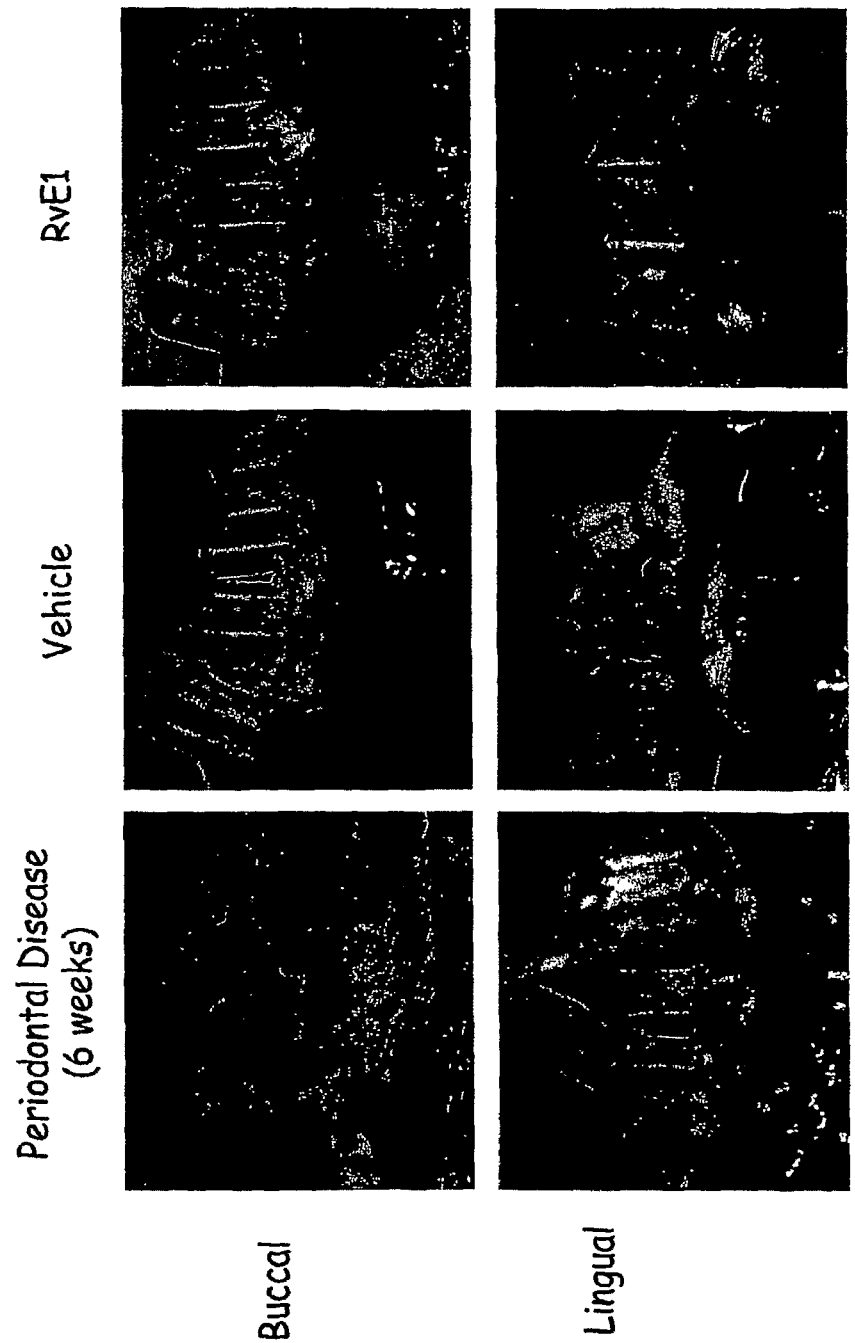
FIG. 2 presents pictures of the buccal and lingual mandibles of rabbits treated, as described in the Examples section, by ligature+*P. gingivalis* (first column), ligature+*P. gingiva-*

FIG. 2 shows the mandibles of rabbits treated either with ligature and topical *P. gingivitis* application alone or ligature and topical *P. gingivitis* application and which then received either topical application of vehicle (i.e., ethanol) alone or topical application of resolvin E1 in ethanol. The soft tissue in the resolvin-treated group was found to be distinctly healthier than the control group. As expected, the disease progressed in those animals treated with vehicle alone. The animals treated with resolvin showed lower soft tissue pocket depth measurements (see FIG. 3). More specifically, there was improvement over baseline. The same results were seen with hard tissue crestal distance measurements (see FIG. 4 and FIG. 5). Unexpectedly, hard-tissue-infrabony pocket depth measurements also showed improvement over baseline (see FIG. 6), as well as measurements of tooth mobility (see FIG. 7), leading to the conclusion that resolvin assisted in deposition of bone (i.e., bone growth).

Other Embodiments

Other embodiments of the invention will be apparent to those skilled in the art from a consideration of the specification or practice of the invention disclosed herein. It is intended that the specification and Examples be considered as exemplary only, with the true scope of the invention being indicated by the following claims.

What is claimed is:

1. A method of growing bone in a vertebrate subject suffering from bone loss as a result of periodontal disease, the method comprising a step of topically administering to the oral cavity of the subject an effective amount of Resolvin E1.

2. The method of claim 1, wherein the method results in an increase of bone mass, an increase of bone density, or a combination thereof.

3. The method of claim 1, wherein the vertebrate subject is a human patient.

4. The method of claim 1, wherein said method further comprises a step of administering to the subject an effective amount of a therapeutic agent that promotes bone growth or inhibits bone resorption.

5. The method of claim 4, wherein the step of administering said resolving and the step of administering said therapeutic agent that promotes bone growth or inhibits bone resorption are performed sequentially.

6. The method of claim 4, wherein the step of administering said resolvin and the step of administering said therapeutic agent that promotes bone growth or inhibits bone resorption are performed simultaneously.

7. The method of claim 4, wherein said therapeutic agent that promotes bone growth or inhibits bone resorption is selected from the group consisting of bone morphogenetic factors, anti-resorptive agents, osteogenic factors, cartilage-derived morphogenetic proteins, growth hormones, estrogens, bisphosphonates, statins, differentiating factors, and combinations thereof.

* * * * *